(12) United States Patent
Schouten et al.

(10) Patent No.: US 9,878,034 B2
(45) Date of Patent: *Jan. 30, 2018

(54) ADJUVANTED VACCINE FORMULATIONS

(75) Inventors: Govert Johan Schouten, Leiderdorp (NL); Cornelis Johannes Leenhouts, Haren (NL)

(73) Assignee: MUCOSIS B.V., Groningen (NL)

( * ) Notice: Subject to any disclaimer, the term of this patent is extended or adjusted under 35 U.S.C. 154(b) by 349 days.

This patent is subject to a terminal disclaimer.

(21) Appl. No.: 13/499,488

(22) PCT Filed: Oct. 1, 2010

(86) PCT No.: PCT/NL2010/050639
§ 371 (c)(1),
(2), (4) Date: May 10, 2012

(87) PCT Pub. No.: WO2011/040811
PCT Pub. Date: Apr. 7, 2011

(65) Prior Publication Data
US 2012/0219586 A1 Aug. 30, 2012

(30) Foreign Application Priority Data

Oct. 2, 2009 (EP) .................................. 09172099

(51) Int. Cl.
| | | |
|---|---|---|
| *A61K 39/145* | (2006.01) |
| *A61P 31/04* | (2006.01) |
| *A61K 39/29* | (2006.01) |
| *A61K 35/74* | (2015.01) |
| *A61K 39/39* | (2006.01) |
| *A61K 39/12* | (2006.01) |
| *A61K 39/00* | (2006.01) |

(52) U.S. Cl.
CPC ............ *A61K 39/292* (2013.01); *A61K 35/74* (2013.01); *A61K 39/12* (2013.01); *A61K 39/145* (2013.01); *A61K 39/39* (2013.01); *A61K 39/00* (2013.01); *A61K 2039/543* (2013.01); *A61K 2039/545* (2013.01); *A61K 2039/5555* (2013.01); *A61K 2039/55594* (2013.01); *C12N 2730/10134* (2013.01); *C12N 2760/16134* (2013.01)

(58) Field of Classification Search
CPC ........ A61K 39/00; A61K 39/12; C07K 14/47; C12Q 1/6883
See application file for complete search history.

(56) References Cited

U.S. PATENT DOCUMENTS

| | | | | |
|---|---|---|---|---|
| 6,136,606 A * | 10/2000 | Chatfield | ................... | 424/206.1 |
| 6,896,887 B2 * | 5/2005 | Leenhouts et al. | ......... | 424/234.1 |
| 9,011,870 B2 * | 4/2015 | Leenhouts | ........... | C07K 14/335 424/193.1 |
| 2009/0081253 A1 | 3/2009 | Hanon et al. | | |

FOREIGN PATENT DOCUMENTS

WO 9610421 4/1996

OTHER PUBLICATIONS

Audouy et al. (Vaccine, 2006, p. 5434-5441 in IDS on Apr. 13, 2012).*
Catriona R. Crawford, et al., The effect of bacterial peptidoglycans on the immune response of hamsters to influenza virus vaccines, Clin. exp. Immunol. (1982) 48, 739-746.
Audouy et al., "Lactococcus Lactis GEM Particles Displaying Pneumococcal Antigens Induce Local and Systemic Immune Responses Following Intranasal Immunization", Vaccine, vol. 24, No. 26, pp. 5434-5441; 2006.
Audouy et al., "Development of Lactococcal GEM-based Pneumococcal Vaccines", Vaccine, vol. 25, No. 13, pp. 2497-2506; 2007.
van Roosmalen et al., "Mucosal Vaccine Delivery of Antigens Tightly Bound to an Adjuvant Particle Made from Food-Grade Bacteria", Methods, vol. 38, No. 2, pp. 144-149; 2006.
Bosma et al., "Novel Surface Display System for Proteins on Non-Genetically Modified Gram-Positive Bacteria", Applied and Environmental Microbiology, vol. 72, No. 1, pp. 880-889; 2006.
Anonymous, "Mucosis B.V. and TNO Announce Flue Vaccine Research and Development Partnership", Online, XP-002569981, Retrieved from the Internet: URL:http://www.mucosis.com/files/Mucosis%20receives%20key%20US%20patent.pdf, the whole document; 2010.
Anonymous, "Mucosis Receives Key US Patent Covering its Mimopath Technology", Online, XP-002569982, Retrieved from the Internet: URL:http://www.mucosis.com/files/Mucosis%20receives%20key%20US%20patent.pdf, the whole document; 2009.
Ogunniyi et al., "Development of a Vaccine against Invasive Pneumococcal Disease Based on Combinations of Virulence Proteins of *Streptococcus pneumoniae*", Infection and Immunity, vol. 75, No. 1, pp. 350-357; 2007.
McCool et al., "Serum Immunoglobulin G Response to Candidate Vaccine Antigens during Experimental Human Pneumococcal Colonization", Infection and Immunity, vol. 71, No. 10, pp. 5724-5732; 2003.
Zhang et al., "Immune Responses to Novel Pneumococcal Proteins Pneumolysin, PspA, PsaA, and CbpA in Adenoidal B Cells from Children", Infection and Immunity, vol. 70, No. 10, pp. 5363-5369; 2002.
Saluja et al., "Intranasal Delivery of Influenza Subunit Vaccine Formulated with GEM Particles as an Adjuvant", The AAPS Journal, pp. 1-8; 2010.

(Continued)

*Primary Examiner* — Agnieszka Boesen
(74) *Attorney, Agent, or Firm* — NLO N.V.; Catherine A. Shultz; Minerva Rivero

(57) ABSTRACT

The invention relates to adjuvanted vaccine formulations, in particular influenza vaccines for intranasal delivery. Provided is an adjuvanted influenza vaccine formulation, comprising (i) peptidoglycan microparticles obtained from a Gram-positive bacterium and (ii) at least one influenza virus antigen or antigenic preparation thereof, which antigen or antigenic preparation is not fused or otherwise covalently attached to a proteinaceous peptidoglycan binding moiety.

12 Claims, 10 Drawing Sheets

(56) References Cited

OTHER PUBLICATIONS

Figure 1:
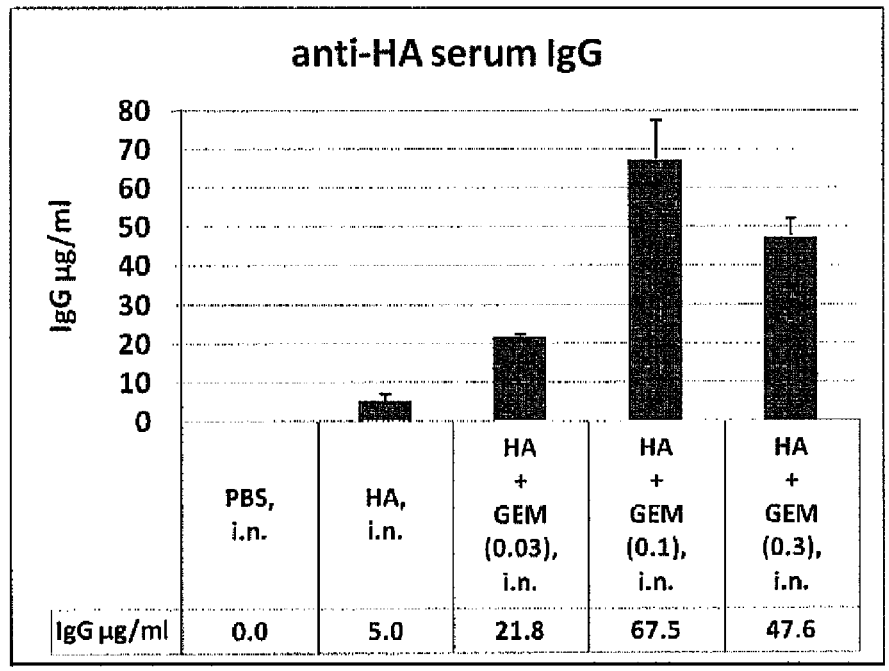

Ramirez et al., "Neonatal Mucosal Immunization with a Non-Living, Non-Genetically Modified Lactococcus Lactis Vaccine Carrier Induces Systemic and Local TH1-type Immunity and Protects Against Lethal Bacterial Infection", NIH Public Access, Online, pp. 1-23; 2010.

* cited by examiner

ADJUVANTED VACCINE FORMULATIONS

This application is the U.S. National Phase of, and Applications claim priority from, International Patent Application Number PCT/NL2010/050639 filed 1 Oct. 2010 and European Patent Application Number 09172099.5 filed 2 Oct. 2009 which are incorporated herein by reference in their entirety.

BACKGROUND OF THE INVENTION

The invention relates to adjuvanted vaccine formulations, in particular influenza vaccines capable of mounting a mucosal immune response e.g. upon intranasal or intramuscular delivery.

Seasonal influenza is still one of the major causes for mortality and morbidity worldwide. Annual vaccinations are the most effective strategy to prevent and control influenza infections. Seasonal influenza vaccines are prepared based on the prediction of the expected strain of epidemic of the next season. These are parenterally injected vaccines that do not prevent the infection itself, which would reduce the severity and complications after the infection. Parenteral vaccines can induce the neutralizing IgG antibody in the serum but they cannot induce the secretory IgA antibody which acts on the mucosal surface. In contrast, intranasal (i.n.) vaccines may induce both a systemic and mucosal immune response. Secretory IgA antibodies on the mucosal membrane surface are highly effective for preventing infection because they react on the surface of the mucosal membrane before the pathogens attach to the epithelial cell surface, which is the first target of influenza viral infection. Moreover, serum IgG antibodies are less effective against drifted viral strains because they act more specifically than secretory IgA antibodies. Secretory IgA antibodies have cross-protective effects against variant strains of the influenza virus. The exact mechanism of the cross-reactive effects of IgA is still unknown, but this phenomenon is a great advantage in preventing infection. Influenza displays an extraordinary capacity to change the antigenic characteristics of its two major membrane proteins, hemagglutinin (HA) and neuraminidase (NA). This occurs by the continuous selection away from the adaptive immune response established in the human population. Due to the high mutation rate of the virus, a particular vaccine formulation usually works for only about a year. The World Health Organization coordinates the contents of the vaccine each year to contain the most likely strains of the virus to attack the next year. Nowadays, conventional vaccines are vaccines consisting of three inactivated influenza viruses (two A-strains and one B). This trivalent influenza vaccine is re-formulated annually, based on influenza strains projected by the WHO to be prevalent in the upcoming flu season. For example, the annually updated trivalent flu vaccine for the 2007-2008 season consists of hemagglutinin (HA) surface glycoprotein components from influenza H3N2, H1N1, and B influenza viruses.

Other advantages of i.n. delivery of vaccines is that delivery of the vaccine does not require trained health care personnel for the administration of vaccine, rendering this type of vaccines suitable for people with needle-phobia and circumvents the problem of needle stick injuries. Furthermore, it is reported that the mucosal immune system develops early in life and is not affected by aging (McElhaney J E. Vaccine 2005 Jul. 8; 23 Suppl 1:S10-25; Szewczuk M R et al. Ann N Y Acad Sci 1983 Jun. 30; 409:333-44). Therefore, a concomitant advantage of e.g. intranasal influenza immunization is that it can potentially provide effective immunity in all age groups and can be used for mass vaccination. Various concepts for immunization against influenza via the nasal or oropharyngeal route and using inactivated influenza antigen have been explored as needleless alternatives to the subcutaneous or intramuscular immunization. Experimental data supportive for needle-less approaches have been generated in animal models. Concepts using inactivated influenza antigen (such as chemically inactivated whole virus particles, or further processed viral components such as split virus, or purified surface antigens haemagglutinin (HA) and/or neuraminidase (NA)) for immunization via the intranasal route that are supported by animal data include either the use of an adjuvant or immune stimulator in combination with the inactivated influenza antigen, or require multiple vaccination. An adjuvant is any substance that enhances the immunogenicity of antigens mixed with it. In humans successful vaccination against influenza via the intranasal route has only been reported for (a) live (cold adapted strains) influenza vaccines (FluMist™, MedImmune Vaccines Inc), (b) virosomal influenza vaccine adjuvanted with the heat labile toxin of *E. coli* (NasalFlu, Berna Biotech Ltd) or (c) using high amounts of antigen and repeated vaccination. Although live vaccines are capable of inducing a satisfactory immune response, their specific nature of being a live virus causes additional safety concerns, and is likely to induce side effects due to the required viral replication round in the upper respiratory tract. Also the required storage conditions are limiting the commercialization of these products. A strong association between the use of the intranasal influenza vaccine with *E. coli* HLT as adjuvant, and facial paralysis (Bell's Palsy), led to withdrawal of the HLT adjuvanted virosomal vaccine from the market.

Currently, live attenuated influenza virus vaccines (LAIV) are marketed for i.n. administration. LAIV vaccines have shown to induce both systemic and mucosal immune response. However, LAIV vaccine is licensed by the FDA only for persons aged 2-49 years and not for use in high risk populations (elderly, children and chronically ill patients) (Centers for Disease Control and Prevention. http://www.cdc.gov/flu/professionals/vaccination/pdf/targetpopchart.pdf; Belshe R B et al. Vaccine 2008 Sep. 12; 26 Suppl 4:D10-6). However, most of the marketed influenza vaccines are inactivated vaccines which can be administered safely via i.n. route to the whole population. A disadvantage of these vaccines is that they have shown to be poorly immunogenic when administered via this route (Vaccine 2007 Jul. 20; 25 (29):5367-73; Eyles et al., BioDrugs 2000 January; 13(1):35-59).

To increase the immunogenicity, inactivated influenza vaccines require adjuvants to potentiate the immune response when administered via the i.n. route. Several adjuvants are currently under development for i.n. immunizations like virus like particles (Matassov D et al. Viral Immunol 2007 September; 20(3):441-52), ISCOMS (Sjolander S et al. Vaccine 2001 Jul. 16; 19(28-29):4072-80), lipids, nucleic acids (Joseph et al. Vaccine 2006 May 1; 24(18):3990-4006) and bacterial components (Haan et al. Vaccine 2001 Apr. 6; 19(20-22):2898-907; Plante et al. Vaccine 2001 Oct. 12; 20(1-2):218-25). However, the development of many of these adjuvants systems is hampered by safety and regulatory concerns. For example potent bacterial adjuvants like LT (heat liable toxin of *E. coli*) have shown severe side effects in humans (Mutsch et al. N Engl J Med 2004 Feb. 26; 350(9):896-903). The inclusion of aluminium salt adjuvants as has been suggested for influenza vaccines not only requires extra mixing steps during manufacture, thereby slowing down overall manufacture, but inclusion of these salts is associated with various problems. For example, their insolubility means that adsorbed antigens settle from suspension, so preparation of individual doses from bulk vaccine requires extra care. In addition, binding of antigen to the salts complicates quality control of the final vaccines. In particular, some potency tests for influenza vaccines are based on in vitro immunoassays that require unbound antigen i.e. adsorption to the adjuvant means that these tests cannot be used. Recently, much emphasis is put on the phenotype of the immune response i.e. Th1, Th2 or balanced response. Subunit vaccine administered via the i.n. route and many of the nasal adjuvants like chitosan, ISCOMS, lipids, and LT induce a mixed Th1/Th2 type response. However, a Th1 response is considered to be superior to Th2 or a mixed response because it 1) results in better protection from infection; and 2) helps in virus neutralization by secretion of INF-γ. Moreover, the natural infection also induces a Th1 type of response. In addition, secretory IgA antibodies on the mucosal membrane surface are highly effective for preventing infection and, importantly, secretory IgA antibodies have cross-protective effects against variant strains of the influenza virus and the mucosal immune system develops early in life and is not affected by aging.

Thus, there is a clear need for an adjuvant which is potent, safe for human use and that can easily be approved by regulatory agencies. Preferably, a vaccine capable of inducing a mucosal immune response like secretory IgA antibodies and/or a response skewed towards Th1 type immunity is desirable. It is therefore an object of the invention to provide further and improved adjuvanted influenza vaccines (for both pandemic and interpandemic use), preferably a vaccine being suitable for intranasal and/or intramuscular delivery. A further aim is to provide a flexible method for influenza vaccine preparation that allows for a convenient and cost-effective annual re-formulation.

DESCTIPTION OF THE INVENTION

It was found that the above goals can be met by co-formulating antigen with inactivated peptidoglycan particles that are obtained from Gram-positive bacteria. The particles are not only highly effective to enhance the immunogenicity of intranasally administered subunit vaccine but also induce secretory IgA and modulate the response from a balanced to a Th1-skewed immune response. Intranasal delivery induced a comparable systemic immunity and even a superior mucosal and cell-mediated immunity when compared to conventional intramuscular immunization with subunit influenza virus alone. The protective effect could be achieved by the simple mixing of antigen and the bacterial particles.

Accordingly, the invention relates to an adjuvanted vaccine formulation, comprising (i) peptidoglycan microparticles obtained from a Gram-positive bacterium and (ii) at least one antigen or antigenic preparation thereof, which antigen or antigenic preparation is not fused or otherwise covalently attached to a proteinaceous peptidoglycan binding moiety. Any known or yet to be discovered protective antigen(s) or antigenic fragment(s) thereof, e.g. of viral, bacterial, parasitic, fungal or yeast origin, may be included.

In one embodiment, the antigen is a viral antigen, such as hepatitis B surface antigen or an influenza virus antigen.

In another embodiment, the formulation comprises a bacterial antigen, preferably at least two bacterial proteinaceous antigens or antigenic preparation thereof, which antigen or antigenic preparation is not fused or otherwise covalently attached to a proteinaceous peptidoglycan binding moiety. Any known or yet to be discovered protective combination of two or more proteinaceous antigens or antigenic fragments thereof may be included, such as combinations of the *Streptococcus pneumoniae* antigens PpmA, SlrA, IgA1 protease, PspA, CbpA, PdBD or others or combinations of *Yersinia pestis* antigens LcrV, F1, FliC or combinations of type III secretion pathway antigens such as LcrV, IpaB and D, SipB and D, YopD of *Salmonella typhimurium, Yersinia enterocolitica, Shigella* or combinations of LT and ST antigens of enterotoxic *Escherichia coli* (ETEC) or of other bacterial proteinaceous antigens. In one aspect, the invention provides a protective formulation comprising PspA, CbpA and/or PdBD. Of particular interest is a pneumococcal trivalent vaccine formulation of the invention wherein the bacterial proteinaceous antigens are PspA, CbpA and PdBD. Upon mixing with peptidoglycan microparticles obtained from a Gram-positive bacterium, this cocktail of 3 antigens was found to confer a very good protection in an intranasal challenge mice model of *Streptococcus pneumoniae* infection. Surprisingly, the protective activity after mixing was higher than when the antigens were bound to the particles via fusion to a proteinaceous peptidoglycan binding moiety (See Example 12 and FIG. 16 herein below). Also, the particular combination of antigens appears of relevance for the protective activity since a pentavalent formulation comprising the antigens PpmA, IgA1 protease, PspA, CbpA and PsaA was relatively low when admixed with peptidoglycan particles as compared to the antigens being bound. See Example 13 and FIG. 17.

In a further embodiment, the formulation comprises at least one parasitic antigen or antigenic preparation thereof, which antigen or antigenic preparation is not fused or otherwise covalently attached to a proteinaceous peptidoglycan binding moiety. Any known or yet to be discovered protective parasitic antigen or antigenic fragment thereof may be included, such as circumsporozoite surface antigen or merozoite surface antigen of *Plasmodium falciparum.* Exemplary protective fungal antigens include antigens of *Coccidioides* ssp. Suitable yeast antigens are antigens of *Candida* ssp. Also provided is an adjuvanted vaccine formulation, comprising peptidoglycan microparticles obtained from a Gram-positive bacterium and at least one polysaccharide antigen or antigenic preparation thereof, which antigen or antigenic preparation is not fused or otherwise covalently attached to a proteinaceous peptidoglycan binding moiety. Any known or yet to be discovered protective polysaccharide antigen or antigenic fragment thereof may be included, such as the *Streptococcus pneumonia, Haemophilus influenza, Neisseria meningitides, Staphylococcus aureus* capsular polysaccharides or other polysaccharides.

In a preferred embodiment, the invention provides an adjuvanted influenza vaccine formulation, comprising (i) peptidoglycan microparticles obtained from a Gram-positive bacterium and (ii) at least one influenza virus antigen or antigenic preparation thereof, which antigen or antigenic preparation is not fused or otherwise covalently attached to a proteinaceous peptidoglycan binding moiety. In another embodiment, the invention provides an adjuvanted hepatitis B vaccine formulation, comprising (i) peptidoglycan microparticles obtained from a Gram-positive bacterium and (ii) at least one hepatitis B virus antigen, e.g. a viral envelope protein such as hepatitis B surface antigen (HBsAg), or antigenic preparation thereof, which antigen or antigenic preparation is not fused or otherwise covalently attached to a proteinaceous peptidoglycan binding moiety. In yet another embodiment, the invention provides an adjuvanted pneumococcal vaccine formulation, comprising (i) peptidoglycan microparticles obtained from a Gram-positive bacterium and (ii) at least one pneumococcal antigen, preferably PdBD, more preferably PspA, CbpA and PdBD, which antigen is not fused or otherwise covalently attached to a proteinaceous peptidoglycan binding moiety.

Peptidoglycan microparticles for use in a vaccine according to the invention can be obtained by methods known in the art. See for example WO 02/101026 and U.S. Pat. No. 6,896,887 disclosing a method for obtaining cell-wall material of a Gram-positive bacterium comprising treating said cell-wall material with a solution capable of removing a cell-wall component such as a protein, (lipo)teichoic acid or carbohydrate from said cell-wall material wherein said cell-wall material essentially comprises spherical peptidoglycan microparticles. The cell-wall material has not been mechanically disrupted to result in spherical peptidoglycan microparticles reflecting the size and shape of the Gram-positive bacterium. The particles are non-living, deprived of intact surface proteins and intracellular content. The thick peptidoglycan cell wall however remains intact, and provides the structural rigidity to constitute the bacterial shaped peptidoglycan spheres of about 1 µm in size, referred to as Gram-positive enhancer (GEM) particles. A major hurdle in the area of mucosal adjuvant development is to proof their safety in order to obtain approval by regulatory agencies. The particles used in this study are safe to use in comparison to other adjuvants and other lactic acid bacteria systems evaluated for vaccination. During the production of the particles, bacteria are treated with acid, which results in loss of genetic material. The loss of the genetic material is beneficial as the problem of DNA shedding and infection in the mucosal layer by the bacteria is avoided. Moreover, the particles are produced from a bacterium which is used in the production of dairy products and is considered a GRAS organism. GEM particles have already been tested intranasally in rabbits in a preclinical GLP toxicity study and no adverse events were reported. Therefore, GEM particles can be considered as a safe candidate adjuvant for mucosal use in humans.

In one embodiment, a vaccine formulation comprises microparticles obtained from food-grade bacterium, preferably a lactic acid bacterium. Preferably, the microparticles are obtained are obtained from the food-grade bacterium *Lactococcus lactis,* a non-pathogenic, non-colonizing Gram-positive bacterium. Moreover, *L. lactis* is approved for human use by regulatory agencies and considered as a GRAS (generally recognized as safe) organism. In one embodiment, the peptidoglycan particles are produced by heating the *L. lactis* in acid, followed by washing with phosphate buffer (van Roosmalen M L et al. Methods 2006 February; 38(2):144-9.

The particles have been studied as antigen carrier for mucosal vaccination of malarial parasite antigen and pneumococcal antigens because of their improved capacity for binding with a proteinaceous substance comprising a peptidoglycan binding domain (like an AcmA cell wall binding domain or homolog or functional derivative thereof). These studies demonstrated that antigens attached to and displayed on GEM particles induced a higher immune response than antigen alone. It was generally believed in the art that immobilization and optimal surface display of antigen on the carrier particles was important for the adjuvant effect.

The present study surprisingly shows that, in contrast to earlier studies wherein antigens were bound to the particles, the mere admixing of peptidoglycan particles and antigen(s) significantly enhances the antigen's immunogenicity. What is more, in certain cases better protective activities can be achieved upon mixing with particles as compared to attaching/immobilization onto the particles.

The expression "which antigen or antigenic preparation is not fused or otherwise covalently attached to a proteinaceous peptidoglycan binding moiety" as used herein is meant to distinguish the invention from the prior art wherein antigenic moieties are attached to peptidoglycan microparticles by fusion or attaching the antigen to a proteinaceous substance also referred to as "protein anchor" or "Protan" (PA), which typically comprises at least one repeat, but preferably two or three repeat sequences of an AcmA cell wall binding domain or homolog or functional derivative thereof. For example, EP 1395648 discloses methods for binding AcmA-type protein anchor fusions to cell-wall material of micro-organisms. WO 2007/011216 relates to an antigen-loaded immunogenic carrier complex comprising at least one bifunctional polypeptide attached to an immunogenic carrier, said bifunctional polypeptide comprising a peptidoglycan binding domain (PBD) through which the polypeptide is attached to said carrier, fused to an antigen binding domain (ABD) to which at least one antigen of interest is bound.

In a preferred embodiment, the antigen is an influenza virus antigen. As shown herein below, it was surprisingly found that a GEM based i.n. influenza vaccine according to the invention elicited a response biased towards a Th1 phenotype. It was found that intranasally administered subunit vaccine adjuvanted with GEM particles (which are simply mixed with vaccine) can be used in a prime-boost vaccination strategy to induce protective levels of HI titers ($>^2$ log 5.3,), which is considered to be an important correlate of protection. Moreover, the GEM based i.n. influenza vaccine is completely protective after lethal challenge. In addition, the serum IgG results clearly highlights that GEM particles enhance the immunogenicity of the i.n. administered influenza subunit vaccine. In addition to substantial serum responses, the GEM adjuvanted i.n. vaccine elicited a strong mucosal immune response i.e. secretion of the sIgA in the respiratory mucosa. Induction of significant levels of sIgA in nasal mucosa shows that GEM particles act as immunopotentiators in the nasal mucosa. The immune system of the nasal mucosa consists of the nasal-associated lymphoid tissue (NALT). In the NALT, the antigens are taken up by the M-cells and then presented to antigen presenting cells, which in turn present antigen fragments to the underlying B and T cells. This cascade of events is required for the initial innate and adaptive immune response against the influenza virus. Our results show that i.n. immunization with influenza subunit vaccine mixed with GEM particles induced higher sIgA levels in the nasal mucosa than the i.m. and i.n. immunization with vaccine only. The induction of sIgA antibodies in the NALT might be the result of an interaction with TLR-2 (Toll like receptor) of the peptidoglycan present in GEM particles, as it is known that GEM particles act as a TLR-2 agonist in in vitro studies. Furthermore, it is known that GEM particles can activate the maturation of the dendritic cells and macrophages in-vitro (Audouy S A, et al. Vaccine 2007 Mar. 22; 25(13):2497-506). Thus, both the activation of TLR-2 and maturation of the dendritic cells might have contributed to the stronger mucosal immune response.

Recently, much emphasis is put on the phenotype of the immune response i.e. Th1, Th2 or balanced response. A Th1 response is considered to be superior to Th2 or a mixed response because it 1) results in better protection from infection; and 2) helps in virus neutralization by secretion of INF-γ. Moreover, the natural infection also induces a Th1 type of response. However, subunit vaccine administered via the i.n. route and many of the nasal adjuvants like chitosan, ISCOMS, lipids and LT induce a mixed Th1/Th2 type response. In contrast, the i.n. influenza vaccine according to the invention induced a response skewed towards Th1 type. Thus, GEM particles modulate the response from a balanced to a Th1 skewed response. Furthermore, the vaccine formulation presented herein is much more convenient to produce compared to most of the other adjuvant systems which have to be preformulated. The formulation used in these experiments was prepared by ad-mixing the GEM particles with conventional subunit vaccine. GEM particles can be produced in large quantities under sterile conditions and can be stored at ambient temperature for long time. The ease of formulation and administration makes i.n. GEM-influenza subunit vaccine a promising candidate for vaccination in a pandemic as well as in an epidemic situation.

As is demonstrated in Examples 1 to 8, the inventors show that an i.n. influenza vaccine adjuvanted with GEM particles induces a comparable systemic immunity and superior mucosal and cell-mediated immunity compared to i.m. immunization with subunit influenza vaccine alone. In particular, it induces comparable protective levels of immunity as measured by HI titers after the first booster immunization compared to i.m. immunization with subunit influenza vaccine alone. Importantly, it induced higher sIgA levels which are a first line of defense during influenza infection in the upper respiratory tract. Moreover, it elicited a skewed Th1 type immune response which is considered to provide superior protection. In addition, these immune responses were shown to provide complete protection of mice immunized with a GEM-based intranasal influenza vaccine.

Example 7 (FIGS. 9 and 10) demonstrates the efficacy of an orally administered influenza vaccine composition. Example 8 (FIG. 11) shows that also intramuscular GEM-based influenza vaccines vaccine can be used to elicit high sIgA levels in the mucosal lining of the respiratory tract or other mucosal layers. In addition, the intramuscular route can be used for influenza vaccine mixed with GEM particles to significantly increase the potency of the regular intramuscular benchmark vaccine or to reduce the amount of antigen (antigen dose sparing) in a significant way (FIG. 12). GEM particles can be regarded as safe and potent adjuvants for i.n., i.m. or orally delivered influenza vaccine.

Other suitable viral antigens include respiratory syncytial virus (RSV) proteins, for instance the RSV fusion (F) and attachment (G) glycoproteins, or relevant parts or combinations thereof such as a chimeric FG protein (J Virol. 1991 July; 65(7): 3789-3796). RSV infection has been a long-standing and pernicious problem globally, including the United States, Europe, Australia and Japan. It is particularly troublesome in premature infants, young children, and the elderly, and indeed for all individuals with a weakened immune system. It is estimated that about two thirds of children below age 1 and almost all children between age 1 and 4 are infected at least once with RSV, with most recovering without any need for medical attention. However, 5-10% have prolonged severe infection, a factor believed to be predisposing to wheezing and asthma-like symptoms later in childhood. Other interesting antigens to be used in admixture with peptidoglycan particles include Human Immunodeficiency Virus (HIV) proteins, in particular a glycoprotein exposed on the surface of the HIV envelope like gp120, gp140 or gp160. Gp120 is essential for virus entry into cells as it plays a vital role in seeking out specific cell surface receptors for entry.

An adjuvanted influenza vaccine formulation as provided herein comprises at least one influenza virus antigen or antigenic preparation thereof. For instance, it comprises an influenza protein or a fragment thereof and/or a fusion protein comprising an influenza protein or fragment thereof provided that it is not fused to a peptidoglycan binding domain. A heterologous protein of the invention can comprise any influenza antigen of interest, including haemagglutinin antigen (HA), neuramidase antigen (NA) or a combination thereof. Preferably, the influenza antigen is a surface antigen, i.e. not a structural antigen such as ectodomain of influenza matrix protein 2 (M2e). In one embodiment, the influenza antigen is other than M2e. In a specific aspect, the influenza vaccine formulation contains HA and/or NA as influenza antigens. Amino acid sequences of a variety of different influenza HA and NA proteins (e.g., from different subtypes, or strains or isolates) are known in the art and are available in public databases such as GenBank. Preferably, a vaccine formulation comprises at least one HA subtype.

Influenza virus strains for use in vaccines change from season to season. In the current inter-pandemic period, vaccines typically include two influenza A strains (H1N1 and H3N2) and one influenza B strain, and trivalent vaccines are typical. The invention may also use viruses from pandemic strains such as the new 'swine flu' or 'Mexican flu' H1 or other pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the invention may protect against one or more of HA subtypes H1, H2, H3, H4, H5, H6, H7, H8, H9, H10, H11, H12, H13, H14, H15 or H16. For example, in one embodiment the i.n. vaccine formulation contains between 1 to 15 μg of HA per influenza strain.

In a specific aspect, a vaccine formulation comprising an influenza antigen or antigenic preparation thereof from at least two influenza virus strains, at least one strain being associated with a pandemic outbreak or having the potential to be associated with a pandemic outbreak.

The amount of peptidoglycan particles present in a vaccine formulation is preferably sufficient to induce protective levels of haemagglutinin inhibition (HI) titers in a prime-boost vaccination strategy. For example, a vaccine formulation according to the invention may comprise 0.001 to 1 mg, preferably 0.01 to 0.1 mg, microparticles (dry weight) per microgram of influenza virus antigen. Exemplary i.n. vaccine formulations for human use include the following: 0.3-2.5 mg GEMs (dry weight), trivalent HA (egg, cell, recombinant) 3×1-15 μg or monovalent HA (pandemic) 0.1-15 μg, 0.05-0.15 M PBS pH6-8.

A nasal vaccine composition of the present invention can be formulated as a liquid or a powder type composition, particularly, aerosols, drops, inhaler or insufflation according to the administration methods, and powders or microspheres are preferred. A composition for nasal drops can include one or more acceptable excipients such as antiseptics, viscosity regulators, osmotic regulators and buffers. However, the invention is not limited to nasal vaccine formulations. It was surprisingly found that the addition of GEMs potentiated the efficacy to an i.m. HA vaccine. This can lead to dose-sparing strategies. See Examples 8 and 9, FIG. 12. Accordingly, the invention also provides a composition comprising peptidoglycan microparticles and a (conventional) intramuscular HA vaccine preparation. Furthermore, influenza HA mixed with GEMs resulted upon oral administration in protective serum HI titers (Example 7, FIGS. 9 and 10).

A further aspect of the invention relates to a container comprising a vaccine formulation disclosed herein. In one embodiment, it is an intranasal dispensing device, such as a device in the form of an aerosol or a drop delivery system (intranasal spray), optionally provided with instructions for use.

Still further, the invention provides a method for prophylaxis of influenza infection or disease in a subject which method comprises administering to the subject a vaccine formulation as described herein above. Because of its safety, the vaccine formulation is particularly suitable for use in a human high risk population. For example, the invention herewith provides a convenient, safe and reliable method for prophylaxis of influenza infection or disease in the elderly, in children up to 2 years of age, or in chronically ill patients. The prophylactic method may comprises intranasal, oral or intramuscular delivery of the vaccine formulation, preferably intranasal delivery. It is very convenient to use a dispensing device, for example a dispensing device in the form of an aerosol or a drop delivery system.

The administration amount of a vaccine is determined as the amount that is able to induce immune response effectively. For example, the administration frequency of a vaccine to human is once to several times a day and the dosage is 1-250 µg and preferably 2-50 µg.

Vaccines prepared according to the invention may be used to treat both children and adults. Influenza vaccines are currently recommended for use in paediatric and adult immunisation, from the age of 6 months. Thus the patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, immunodeficient patients, patients who have taken an antiviral compound (e.g. an oseltamivir or zanamivir compound, such as oseltamivir phosphate—see below) in the 7 days prior to receiving the vaccine, people with egg allergies and/or people travelling abroad. As will be understood, the vaccines are not suitable solely for these groups, however, and may be used more generally in a population. For pandemic strains, administration to all age groups is preferred.

Also encompassed within the scope of the present invention is a method for providing an influenza vaccine formulation, comprising the steps of (a) providing peptidoglycan microparticles obtained from a Gram-positive bacterium; (b) providing at least one influenza antigen or antigenic preparation thereof; and (c) admixing the microparticles and the antigen(s). Both steps (a) and (b) can be performed using methodology that is known per se in the art. Since step (b) does not require the fusion or attachment of antigen to a peptidoglycan binding domain like Protan, a method of the invention is far more convenient and economically attractive than prior art methods wherein antigen must first be modified (e.g. by fusion to a proteinaceous linker moiety) for it to bind to peptidoglycan microparticles. In contrast, the present invention can be practiced using conventional subunit vaccines as such.

Accordingly, the invention also relates to the use of peptidoglycan microparticles obtained from a Gram-positive bacterium as adjuvant in an influenza vaccine formulation, said formulation comprising an influenza virus antigen that is not fused or otherwise covalently attached to a proteinaceous peptidoglycan binding moiety.

LEGENDS TO THE FIGURES

FIG. 1: HA antigen (H1N1 A/Beijing) specific total serum IgG expressed in µg/ml in mice immunized three times with PBS or HA+different amount of GEM particles (expressed in mg dry weight). The error bars indicate the standard error of mean (SEM).

Figure 2:
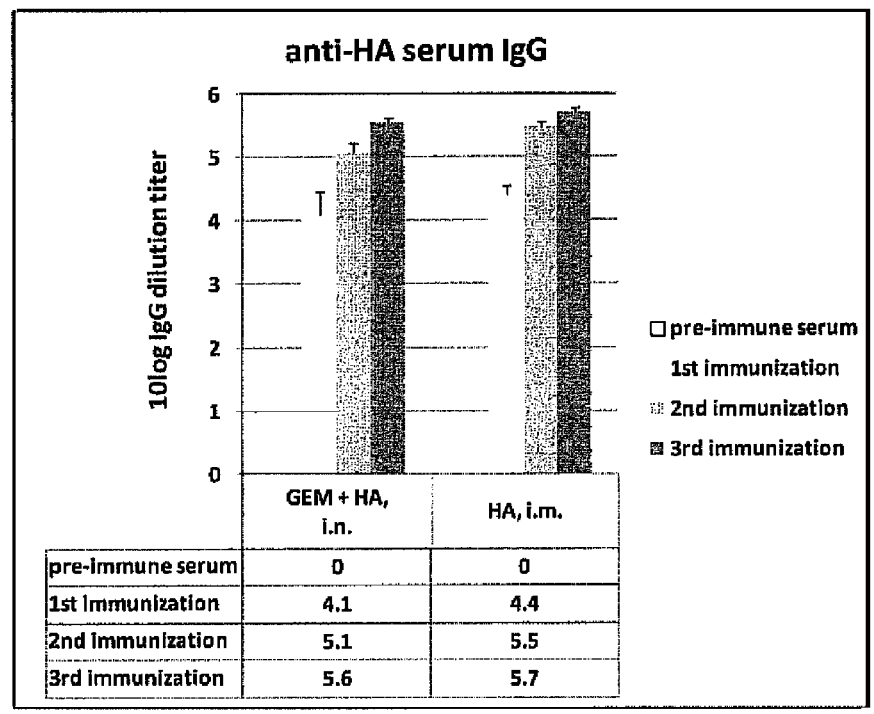

FIG. 2: Comparative analysis of HA antigen (H1N1 A/Beijing) specific total serum IgG dilution titers in different HA groups i.e. i.n. HA+GEM or i.m. HA at 14, 28 and 42 days after the first immunization ($1^{st}$, $2^{nd}$ and $3^{rd}$ immunization, respectively). The error bars indicate the SEM.

Figure 3:
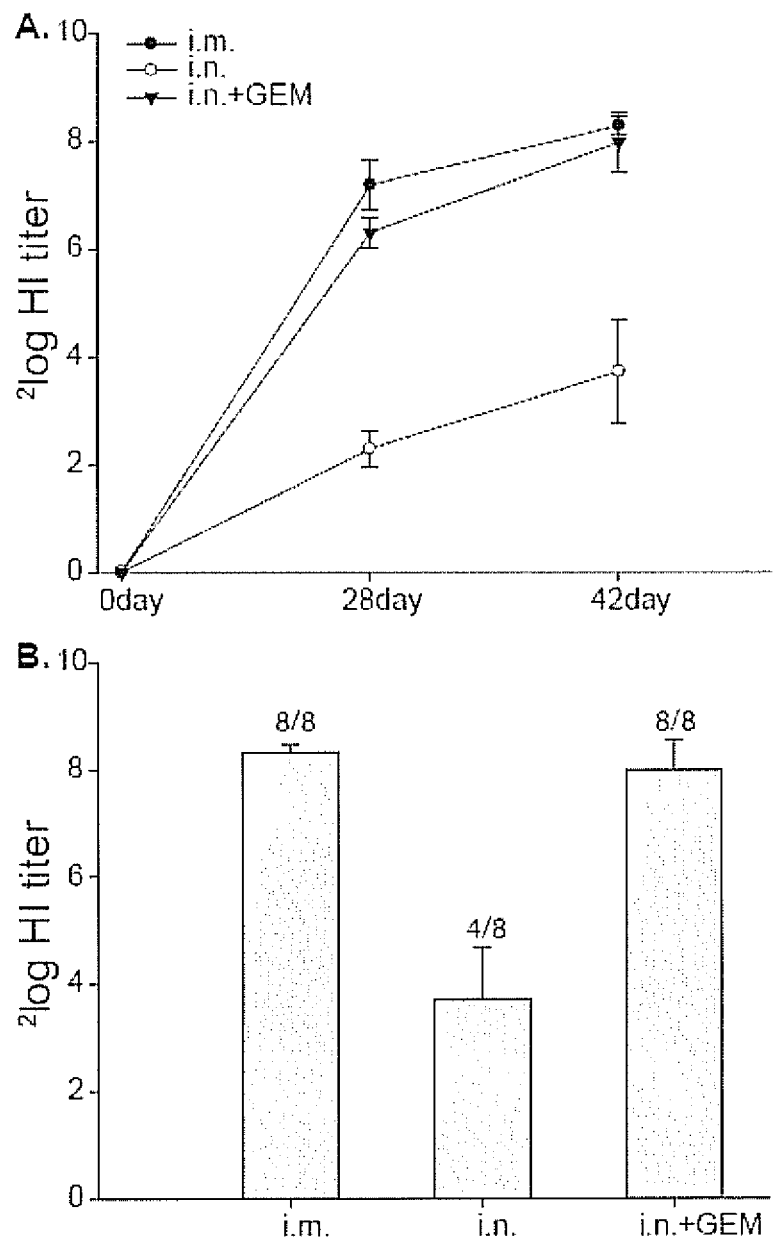

FIG. 3: HA antigen (H3N2 A/Wisconsin) specific HI titers in sera of mice immunized three times. A. Comparative analysis of HI titers in different HA groups i.e. i.m., i.n. and i.n.+GEM at 0, 28 and 42 days after the first immunization. B. Comparative analysis of HI titers between three HA groups i.e. i.m., i.n., i.n.+GEM at 42 days after first immunization. The numbers above the columns indicate the number of responders per group. The error bars indicate the SEM.

Figure 4:
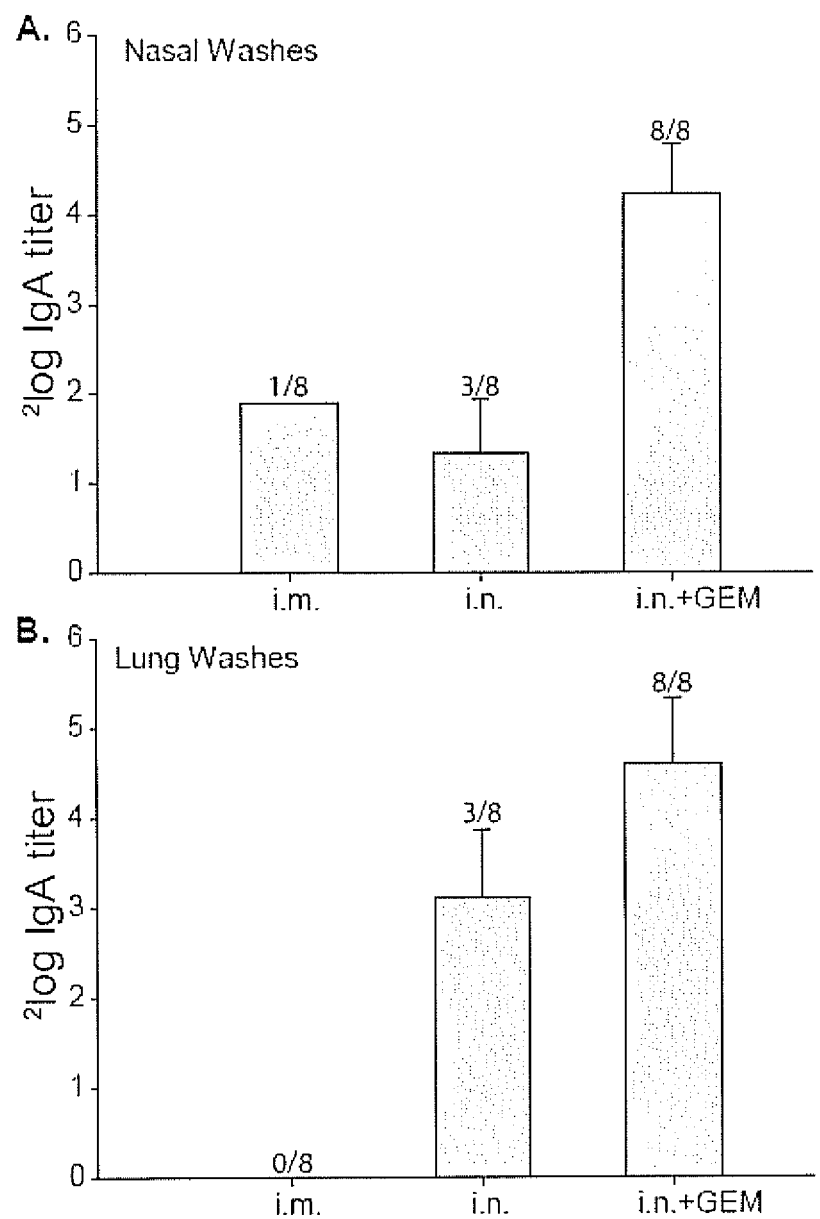

FIG. 4: HA antigen (H3N2 A/Wisconsin) specific sIgA titers in nasal (A) and lung lavages (B) of mice immunized with HA i.m., i.n. or i.n.+GEM. The numbers above the columns indicate the number of responders per group. The error bars indicate the SEM.

Figure 5:
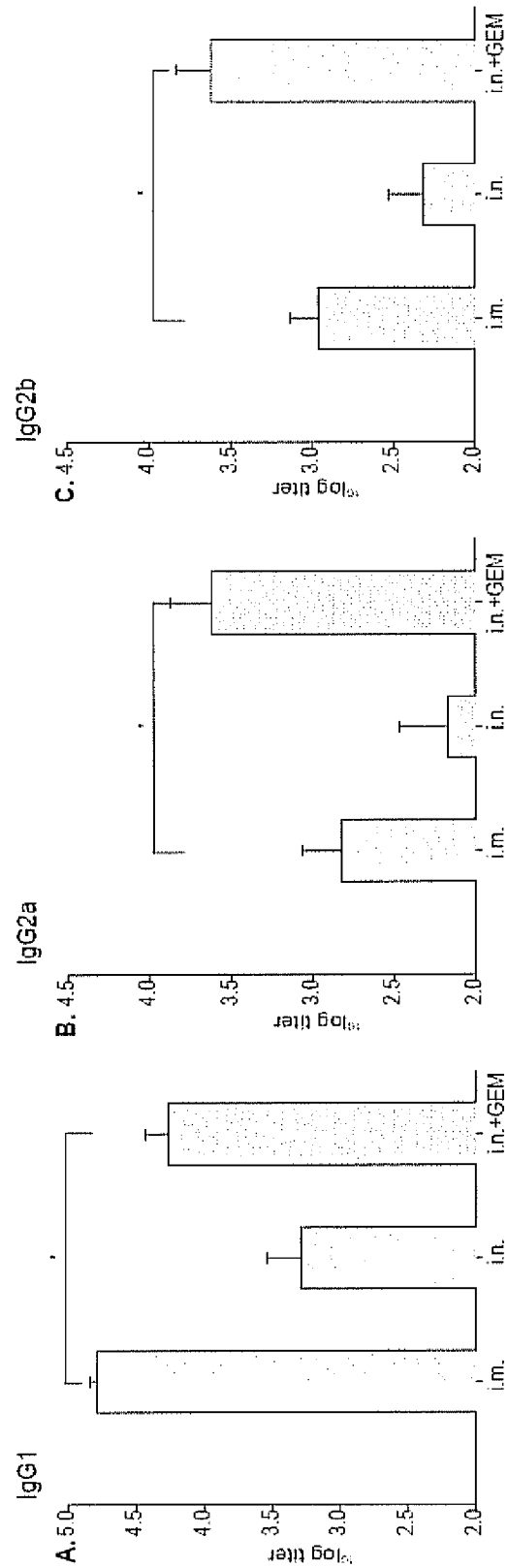

FIG. 5: HA antigen (H3N2 A/Wisconsin) specific IgG subtype titers in sera of mice immunized with HA i.m., i.n. or i.n.+GEM. The IgG1 (A), IgG2a (B) and IgG2b (C) titers were determined. The asterisks mean a P-value<0.05 for the indicated comparison. The error bars indicate the SEM.

Figure 6:
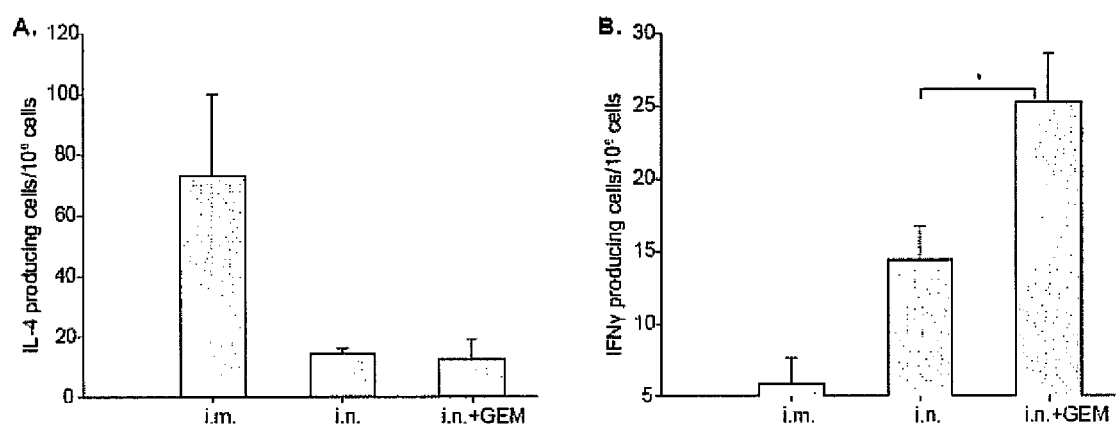

FIG. 6: Cell mediated immune response was determined by determining the cytokine release profile i.e. IL-4 (A), IFNγ (B) in mice immunized with HA i.m., i.n. or i.n.+GEM. The asterisk means a P-value<0.05 for the indicated comparison. The error bars indicate the SEM.

Figure 7:
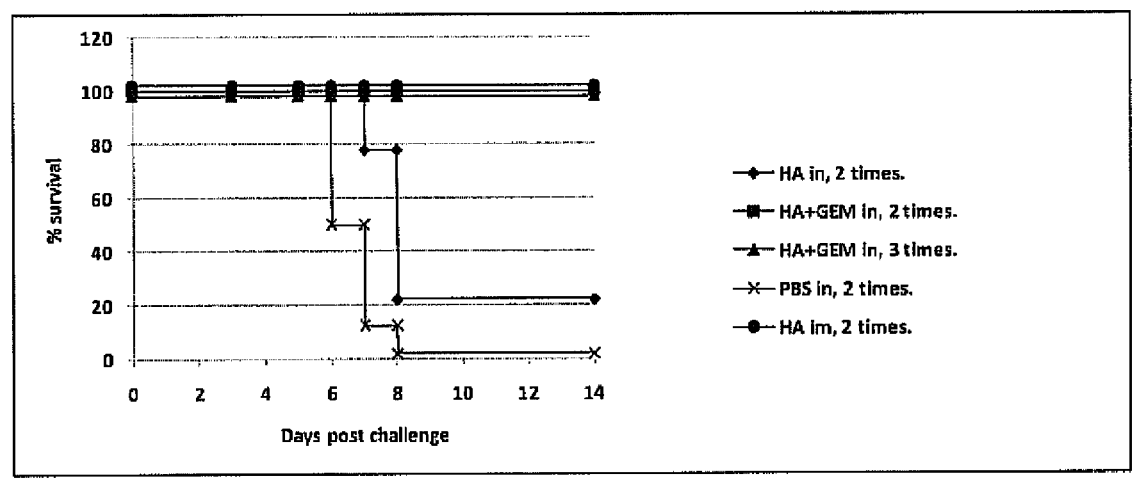

FIG. 7: Survival after challenge (%). Animals were vaccinated with 5 µg HA per dose and GEM containing vaccines were supplemented with 0.3 mg GEM per dose. Animals were challenged 3 weeks after the last booster immunization and followed up for 14 days. Comparative analysis between the five vaccine groups.

Figure 8:
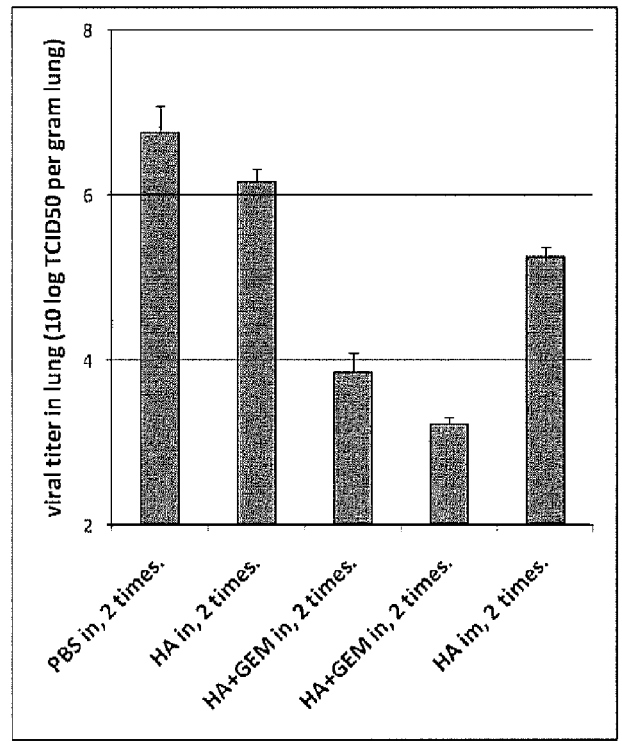

FIG. 8: Viral titres (A/Puerto Rico/8/34 [PR8], TCID50 [Tissue Culture Infectious Dose]) in the lungs after challenge (per gram of lung tissue). Lungs were isolated 4 days post challenge. Comparative analysis between five groups. Standard error of the mean (SEM) is indicated by the error bars.

Figure 9:
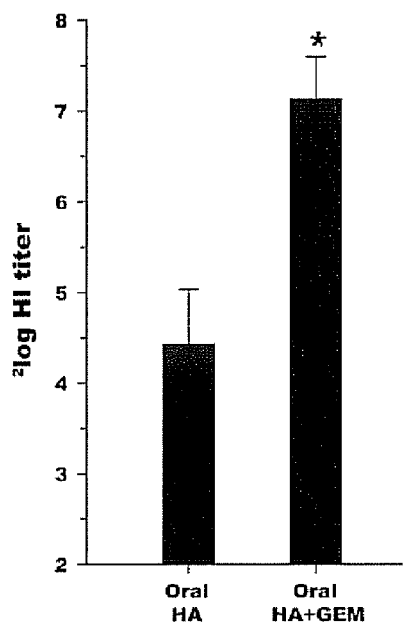

FIG. 9: Subunit antigen (A/Hiroshima [H3N2]) specific serum HI titers in mice immunized with oral HA or oral HA+GEM influenza vaccine. Mice we immunized three times with 20 µg HA per dose. GEM vaccines contained 0.3 mg GEM per dose. * indicates p<0.05. Titers above $^2$Log 5.3 are protective. Standard error of the mean (SEM) is indicated by the error bars.

Figure 10:
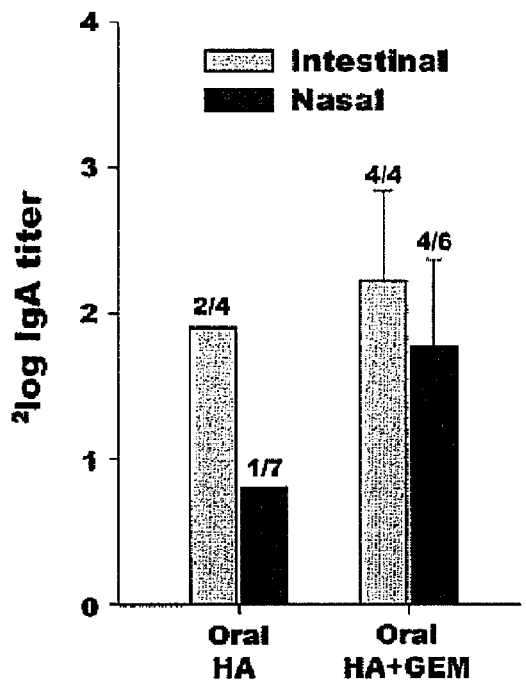

FIG. 10: Subunit antigen (A/Hiroshima [H3N2]) specific sIgA titers in intestinal (grey bars) and nasal lavages (black bars) of mice immunized with oral HA or oral HA+GEM influenza vaccine. The numbers above the columns indicate the number of responders per number of animals analyzed. Standard error of the mean (SEM) is indicated by the error bars.

Figure 11:
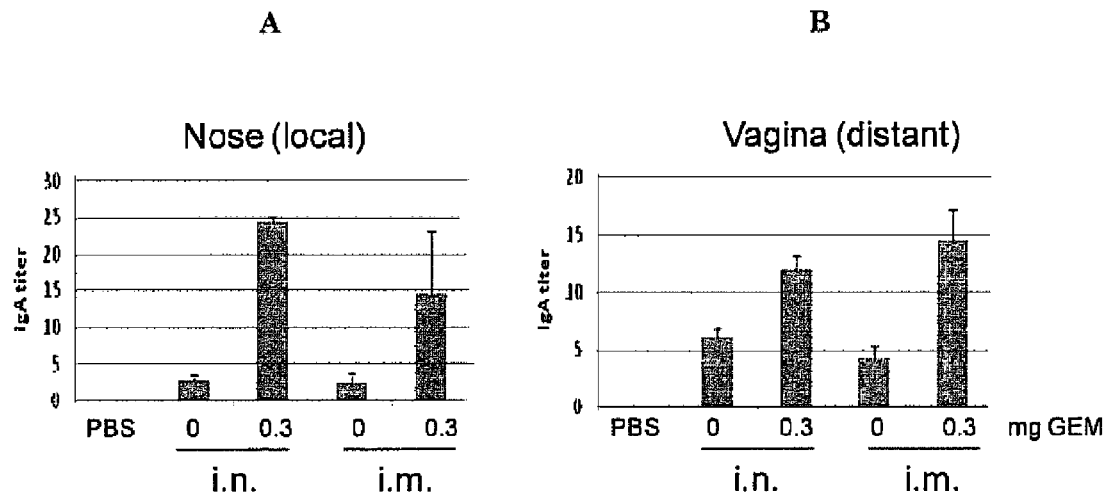
Figure 12:
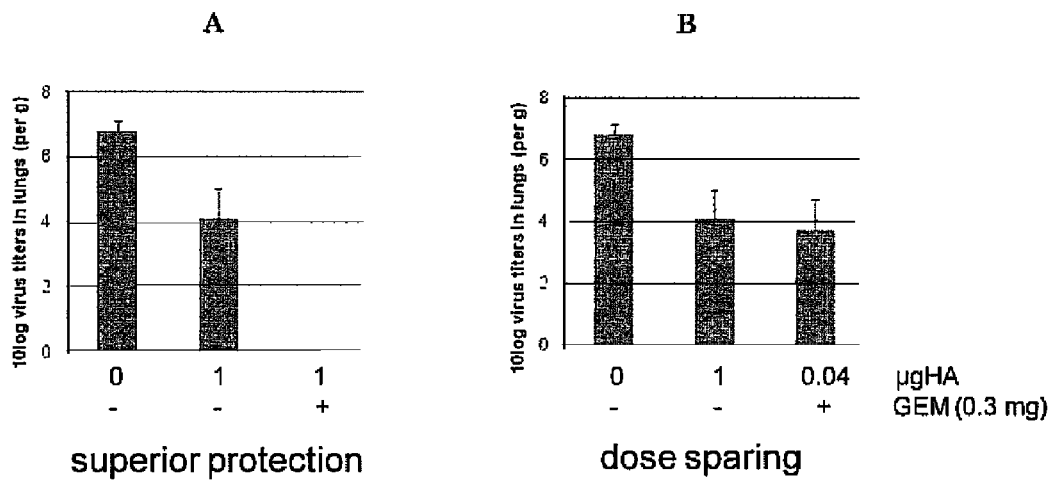

FIG. 11: HA-specific IgA titers in nasal and vaginal washes of female mice that were vaccinated three times (interval 14 days) intranasally (panel A) or intramuscularly (panel B) with a fixed amount of HA (5 µg B/Shangdong/7/97), with or without 0.3 mg GEMs. Wash samples were taken two weeks after the last immunization. Standard error of the mean (SEM) is indicated by the error bars.

FIG. 12: Lung viral titers of mice vaccinated twice with PBS (mock), 1 µg HA (A/PuertoRico/8/34) without GEMs or with 0.04 µg HA (25 times less antigen) formulated with GEM. Two weeks after administration of the final dose, mice were challenged with mouse adapted A/PuertoRico/8/34. Five days post challenge, the animals were sacrificed, lungs were isolated and homogenized and viral titers were determined by endpoint titration on MDCK cells. Standard error of the mean (SEM) is indicated by the error bars.

Figure 13:
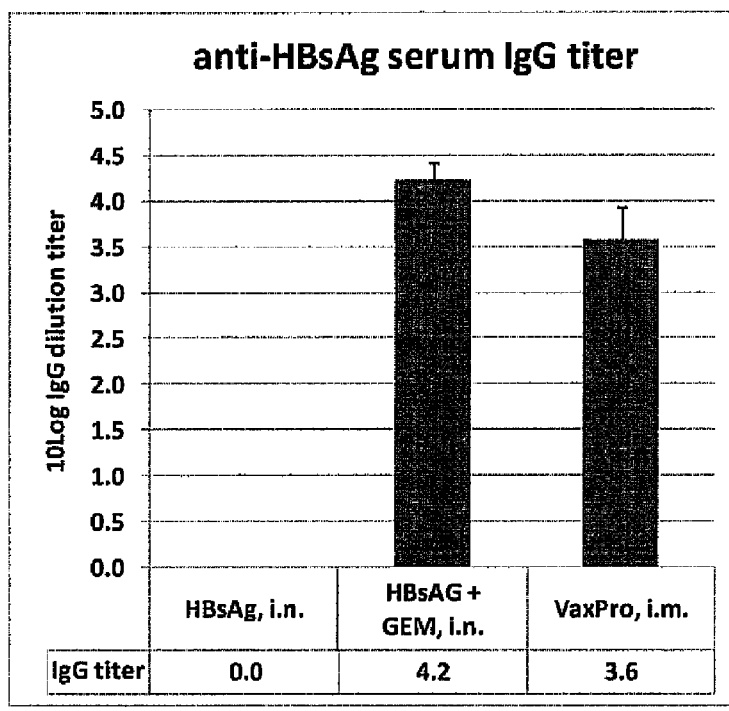

FIG. 13: HBsAg antigen specific IgG dilution titers in sera of C57BL6 mice immunized three times with HBsAg alone (i.n.),+GEM (i.n.) or VaxPro (i.m.). The error bars indicate the SEM.

Figure 14:
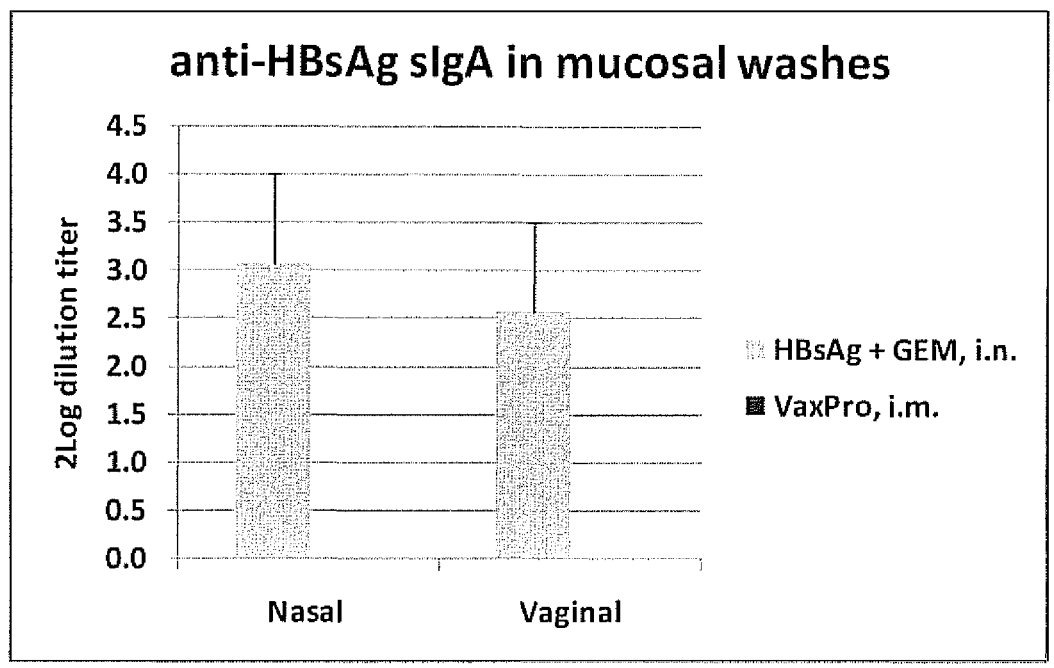

FIG. 14: HBsAg antigen specific sIgA titers in nasal and vaginal lavages of C57BL6 mice immunized three times with HBsAg+GEM (i.n.) or VaxPro (i.m.). The error bars indicate the SEM.

Figure 15:
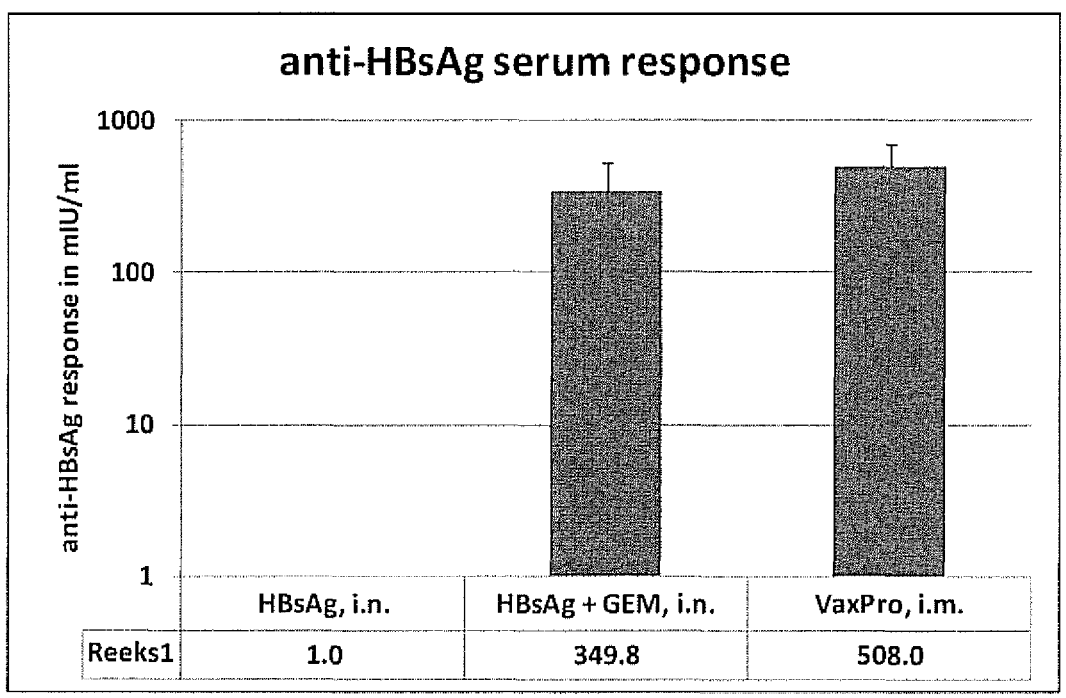

FIG. 15: HBsAg antigen specific serum response measured as mIU/ml of Wistar rats immunized three times with HBsAg alone (i.n.),+GEM (i.n.) or VaxPro (i.m.). A level of ≥10 mIU/ml is considered to be protective. The error bars indicate the SEM.

Figure 16:
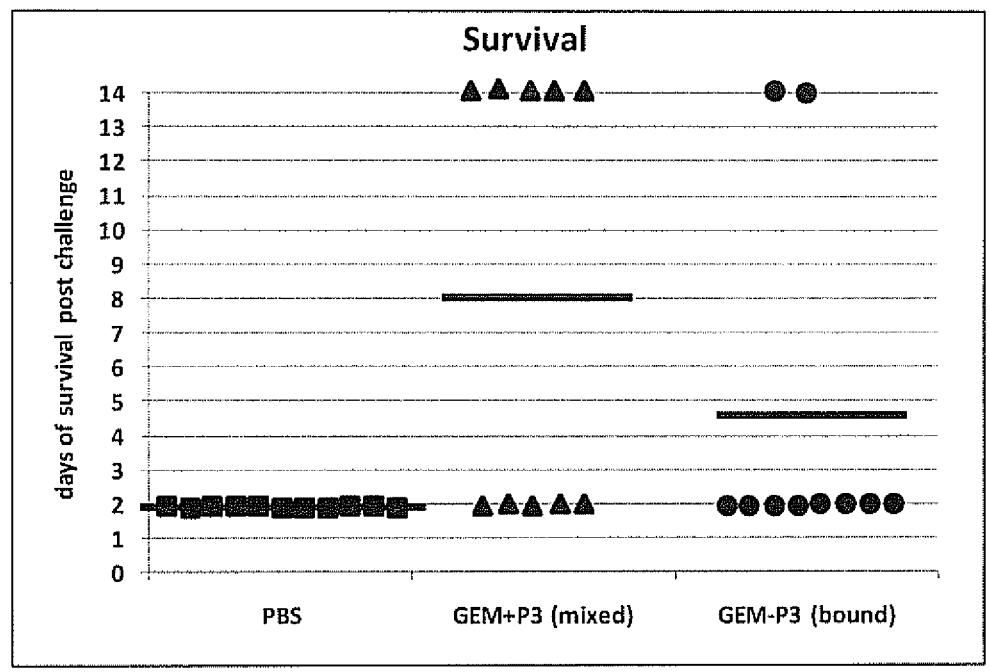

FIG. 16: Survival times in days post challenge. The test materials of all groups were applied intranasally (i.n.). Mice were immunized with PBS (mock immunization), with the pneumococcal P3 proteins (PspA, CbpA, PdBD) mixed with GEM (GEM+P3) or with P3 proteins bound to GEM (GEM-P3). Both vaccines contained 5 µg of each antigen. Each symbol represents 1 animal. The horizontal line indicates the mean.

Figure 17:
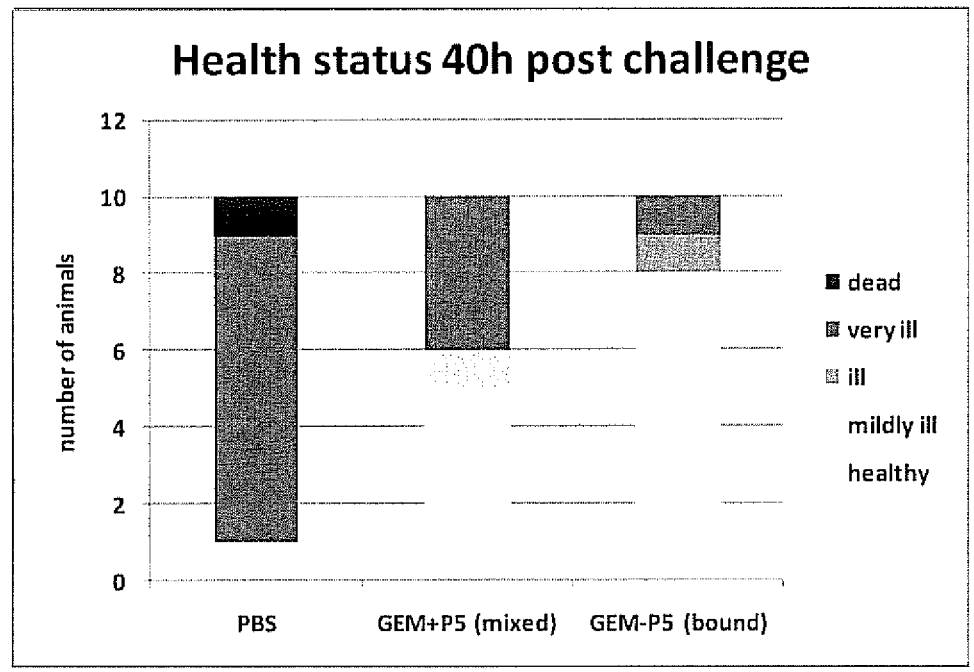

FIG. 17: Health status of mice 40 hrs post intranasal challenge with the virulent *S. pneumonia* strain D39 (serotype 2) that were immunized with PBS (mock immunization), GEM mixed with the P5 proteins (GEM+P5) or GEM with bound P5 proteins (GEM-P5). Vaccines contained 0.5 µg IgA1prt, 3 µg PsaA, 1.5 µg CbpA, 2 µg PpmA, 2 µg PspA and 0.3 mg GEM. The health status 40 h post challenge is a measure for the protectivity of the vaccines.

EXPERIMENTAL SECTION

Materials and Methods

Influenza monovalent subunit vaccine of strain A/Wisconsin (H3N2) derived from eggs and A/Beijing (H1N1) split virus vaccine derived from eggs were used in this study. The concentration of the heamagglutinin (HA) in the vaccine was determined using the single radial immunodiffusion assay.

Recombinant HBsAg (ad/ay) isolated from *Hansenula polymorpha* was used in this study. HBVaxPro from Sanofi Pasteur/MSD was used as the benchmark HBsAg vaccine (40 µg/ml). GEM particles were produced as described before (Van Roosmalen et al., Methods 2006, February; 38(2):144-9).

1.1 Immunizations and Challenges

Animal experiments were evaluated and approved according to the guidelines provided by Dutch Animal Protection Act. Balb/c, C57BL6 mice (6-8 weeks) and Wistar Unilever rats (10 weeks) were purchased from Harlan, The Netherlands. CD 1 mice were purchased from Charles River, Germany. The mice were grouped in 5-10 animals each. The rats groups consisted of 4 animals each. All mice groups were immunized with prime vaccination on day 0 and two booster vaccinations on day 14 and 28 with 5 µg of HA or on day 0 and two booster vaccinations on day 10 and 20 with 5 µg of HBsAg. Intranasal mice immunizations were done with 10 µl of vaccine divided over both the nostrils under inhalation anaesthesia (Isoflurane/$O_2$). Rat groups were immunized with prime vaccination on day 0 and two booster vaccinations on day 10 and 20 with 25 µg of HBsAg. Intranasal rat immunizations were done in a similar way as for the mice with 30 µl of vaccine. Intramuscular mice groups were injected with 50 µl vaccine in posterior thigh muscles under inhalation anaesthesia (Isoflurane/$O_2$). Intramuscular rat groups were injected with 200 µl of vaccine divided over both hind leg muscles. The mice and rats were sacrificed two weeks after the second booster vaccination. After the animals were sacrificed, the spleens of the Balb/c mice were harvested and subsequently stored in supplemented IMDM Glutamax medium with 5% FCS, 1% penicillin/streptomycin and 50 µM β-mercaptoethanol at 4° C. Oral administrations in mice were done 3 times i.e. on day 0, 14 and 28. Briefly, 20 µg subunit vaccine with or without 0.3 mg GEM particles was administered intragastrically in 200 µl of sodium bicarbonate solution (3.2% w/v). The oral administration was performed without anaesthesia using a stainless steel feeding needle.

In challenge experiments, mice immunized with influenza HA vaccines were intranasally challenged (40 µL) 3 weeks post the last booster immunization with 100 plaque forming units (PFU) of strain A/Puerto Rico/8/34 (high dose, 9 animals per group) or 66 PFU of strain A/Puerto Rico/8/34 (low dose, 4 animals per group). Intranasal administration of challenge virus was conducted under light anaesthesia of the animal by aspiration of $O_2$/isoflurane. The animals which received the low dose were sacrificed at 4 post challenge and the lungs were isolated for determination of viral load in the lungs by using an in vitro cell-based assay. In short, MDCK cells together with the viral dilutions were incubated for 1 hour in an incubator (37° C., 5% $CO_2$) and subsequently washed once with PBS. Fresh medium containing trypsine (100 µl medium with 7,5 µg/ml TPCK trypsine) was added to the wells. The cells were incubated for 72 hours in a incubator (37° C., 5% $CO_2$) after which the supernatants were transferred to roundbottom plates (Costar) together with 50 µl 1% (washed) guinea pig erythrocytes. The mixture was incubated for 2 hours at room temperature and the hemagglutination read. The inverse of the highest dilution which still shows hemagglutination is the titer. The animals which received the high dose were followed for clinical signs up to day 14 post challenge and sacrificed unless animals were sacrificed before due to unacceptable suffering (humane endpoint: 10% weight loss on a single day or 15% in multiple days combined with, lethargy, ruffled fur and moribund).

For pneumococcal immunizations CD1 mice received intranasally a dose of 0.01 mL (10 µL) on days 0, 14 and 28. The intramuscular groups received a dose of 0.04 mL (40 µL) on days 0, 14 and 28 injected in the thigh muscle of the hind limbs (alternating left, right and left). Three weeks after the final booster immunizations, mice were challenged with $1 \times 10^6$ CFU *S. pneumoniae* strain TIGR4. Pneumococci were introduced intranasally in a 50 µL inoculum while mice were lightly anaesthesized by inhalation anaesthesia (isoflurane).

Mice were monitored frequently following infection and scored according to their condition based on health status, body weight and body temperature. The bacterial counts in the blood were determined at 40 hours post challenge, and mice that were diseased and needed to be sacrificed (humane endpoint) were sacrificed as well as mice that had more than $5.4 \times 10^3$ CFU/mL in their blood. Remaining mice were sacrificed when they were diseased or at the end of the study (14 days post challenge).

1.2 Sera Collection and Mucosal Washes

Blood samples were drawn three times during the experiments before each vaccine administration and a final bleed was taken at termination 14 days after the last booster administration. Sera were obtained by centrifugation of blood at 1200×g for 5 min and the samples were subsequently stored at −20° C. until further analysis.

Nasal washes were obtained by flushing the nasopharynx with 1 ml PBS (supplemented with protease inhibitors cocktail). Vaginal washes were obtained by flushing the vagina with 100 µl PBS (supplemented with protease inhibitors cocktail). The 100 µl aliquot was withdrawn and reintroduce nine times by using a pipette with a yellow 200 µl tip attached. The wash was transferred to a clean vial and stored at −20° C. Intestinal washes were performed performed by intubating the duodenum via an incision posterior to the stomach using a 1.2 mm×38 mm flexible teflon feeding needle with silicone tip. Before lavage, the jejunum was closed anterior of the ileum with a ligature. Next, a 1-ml syringe was attached to the feeding needle and the lavage was performed by repeated flushing of the duodenum/jejunum with 1 ml of PBS. Immediately after each sample collection, the lavage was mixed with 10 µl stock solution (supplemented with protease inhibitors cocktail) and lavages were kept on ice until further preparation. Lavage samples were centrifuged at 11,000×g for 15 min, and supernatants were collected and stored at 4° C. until further analysis.

1.3 ELISA

The antibody response to HA antigen was determined using ELISA assays to determine serum IgG, IgG1, IgG2a and IgG2b dilution titers, the mucosally secreted sIgA or to determine the amount of HA-specific IgG. For the dilution titers, the plates were incubated with 200 ng of HA/well. After overnight incubation with HA, the plates were blocked with 3% bovine serum albumin (Sigma-Aldrich, Netherlands). Then plates were washed and incubated with sera and mucosal samples in serial dilution for 1.5 h at 37° C. Next, the plates were washed and incubated with horseradish peroxidase-conjugated goat antibodies directed against mouse IgG, IgG1, IgG2a, IgG2b and IgA (Southern Biotech, Birmingham, Ala., USA). Finally, the substrate solution (0.02% 1,2-phenyllendiamin-dihydrochlorid in 50 mM phosphate buffer pH 5.6, containing 0.006% $H_2O_2$) was added and the plates were incubated in the dark for 30 mM at room temperature. The reaction was stopped by addition of 2 M $H_2SO_4$ and absorbance at 490 nm was read with a Benchmark Microplate reader (BioRad, Hercules, Calif.). Titers reported are the reciprocal of the calculated sample dilution corresponding with an A490≥0.2 after background correction.

To determine the amount of HA-specific serum IgG, the microtiter well plates were coated with 200 ng/1000 µl/well H1N1 A/Beijing and with anti-mouse IgG for the calibration curve. After overnight incubation at 4° C., the plates were washed 2 times with coating buffer (0.5 M carbonate-bicarbonate pH9.6-9.8). Blocking was performed with Protifar Plus (2.5% in coating buffer) for 45 mM at 4° C. After washing the plates with coating buffer and PBS/0.05%Tween20 for four times, the sera and the calibration curve were added to the wells. Serial dilutions of sera and the calibration curve (mouse IgG1) were incubated for 1.5 hours at 4° C. Subsequently, plates were washed for three times with PBS/Tween20. The horseradish peroxidase conjugated immunoglobulin (ITK, Southern Biotech), 1:5000 dilution in PBS/Tween20, was added to the wells and incubated for 1 hour at 4° C. After washing the plates three times with PBS/Tween20 and once with water, the plates were stained for 30 minutes using the substrate solution (0.02% 1,2-phenyllendiamin-dihydrochlorid in 50 mM phosphate buffer pH 5.6, containing 0.006% $H_2O_2$) The color reaction was stopped with 2 M $H_2SO_4$. Measurements were performed at 493 nm.

The serum antibody response to HBsAg antigen was determined using ELISA assays to determine IgG dilution titers. For this purpose, ELISA plates coated with 2 µg/ml HBsAg in PBS, 50 µl/well was added and incubated for 1 hour at 37° C. Plates were washed 6× with wash buffer (PBS/0.1% tween20). Plates were blocked with block buffer (PBS/1% BSA), 200 µl/well and incubated for 1 hour at 37° C. Serum samples were serially diluted in block buffer and 50 µl/well was added and incubated for 1 hour at 37° C. Plates were washed 6× with wash buffer. Goat anti-rat IgG conjugated to alkaline phosphatase (Southern Biotech) was used as secondary antibody (diluted 1:3000 in block buffer) and 50 µl/well was added and incubated for 1 hour at 37° C. Plates were washed 6× with wash buffer (PBS/0,1% tween20). p-Nitrophenyl Phosphate Disodium Salt (Calbiochem) in substrate buffer (10 mM diethanolamine/0,5 mM MgCl2 pH 9,5) was used for detection and measurements were done at 405 nm. Titers are expressed as dilution titers, defined as the dilution that shows twice the OD of a pre-immune standard.

HBsAg-specific mucosally secreted sIgA was determined using ELISA assays to determine IgG dilution titers. For this purpose, ELISA plates were coated, washed and blocked as before. Mucosal lavages were serially diluted in block buffer. 50 µl/well was added and incubated for 1 hour at 37° C. Plates were washed 6× with wash buffer. Goat anti-Rat IgA conjugated to horseradish peroxidase (Nordic Immunology) diluted 1:1000 in block buffer was used as secondary antibody and 50 µl/well was added and incubated for 1 hour at 37° C. Plates were washed 6× with wash buffer (PBS/0,1% tween20). TMB (3,3',5,5'-Tetramethylbenzidine, Sigma, Lot 055K8208) was dissolved in 1 ml DMSO and 9 ml of 0.05 M Phosphate-Citrate buffer, pH 5.0 was used for detection. 2 µl of 30% hydrogen peroxide was added per 10 ml of substrate buffer solution, immediately prior to use. The color reaction was stopped with 2 M H2SO4 and measurements were done at 450 nm. Titers are expressed as dilution titers, defined as the dilution that shows three times the OD of the background (HBsAg coating incubated with blocking buffer).

1.4 Haemagglutination Inhibition (HI) Assay

HI titers in serum were determined as described previously [35]. Briefly, serum was inactivated at 56° C. for 30 mM. In order to reduce non-specific haemagglutination, 25% kaolin suspension was added to inactivated sera. After centrifugation at 1200×g, 50 µl of the supernatant was transferred in duplicate to 96 well round bottom plate (Greiner, Alphen a/d Rijn, Netherlands) and serially diluted twofold in PBS. Then 4 haemagglutination units (HAU) of A/Wisconsin influenza inactivated virus were added to each well and the plates were incubated for 40 minutes at room temperature. Finally, 50 µl of 1% guinea pig red blood cells were added to each well and incubated for 2 h at room temperature. The highest dilution capable of preventing haemagglutination was scored as HI-titer.

1.5 HBsAg-Specific Ig Titer Determination with the Abbott AxSYM System

Quantitative determination of antibody against HBsAg expressed in mIU/ml was done on an Abbott AxSYM system, by the AxSYM AUSUB assay. This assay is a microparticle EIA using recombinant HBsAg (ad/ay) on microparticles as the solid phase and biotin coupled to recombinant HBsAg as the conjugate. In the next step, alkaline phosphatase-conjugated anti-biotin is bound to the antigen sandwich. The reaction mixture is transferred to an inert glass fiber matrix to which the microparticles bind irreversibly. Methylumbelliferyl phosphate is used as a substrate, and the fluorescence of the final product, methylumbelliferone, is read by the instrument.

1.6 Elispot

The Elispot assay was performed as described earlier (Amorij J P et al. Vaccine 2007 Dec. 21; 26(1):67-76). Briefly, 96 well microtiter plates (Greiner, Alphen a/d Rijn, Netherlands) were incubated overnight at 4° C. with anti mouse interferon-γ (IFN-γ) and interleukin-4 (IL-4) (B D, Pharmingen, Erembodegem, Belgium). After washing the plates three times with PBS/Tween (Sigma-Aldrich, Netherlands) they were blocked (PBS+4% BSA) for 1 hr at 37° C., spleen cells were added to the plates in concentration $1 \times 10^6$ cells/well with or without subunit vaccine as a stimulation peptide. After incubation overnight at 37° C., 5% $CO_2$, the cells were lysed with cold water. Next, the plates were washed five times with PBS/Tween and incubated with biotinylated anti-mouse IFN-γ and IL-4 antibodies (B D Pharmingen) in concentration of 0.125 μg/ml in PBS+2% BSA. After washing the plates were incubated with Streptavidin alkaline phophatase (BD Pharmingen) for 1 hr at 37° C. Finally, after washing three times with PBS/Tween and two times with PBS, the spots were developed using the substrate solution consisting of 1 mg/ml 5-bromo-4-chloro-3-indolylphophate, 0.92% w/v 2-amino-2-methyl-1-propanol, 0.08 μl/ml TritonX-405, 1 M $MgCl_2$ and 6 mg/ml agarose. The spots were counted using an Elispot reader (A.EL.VIS Elispot reader).

1.7 Statistical Analysis

Statistical analyses were performed using Student's t-test or a nonparametric ANOVA test with p<0.05 as the minimal level of significance. The results are presented as mean±standard error mean (SEM) unless indicated otherwise.

EXAMPLES

Example 1 Adjuvant Effect of GEMs in Intranasal HA Vaccines

The enhancement of the systemic serum antibody response towards intranasal HA (5 μg H1N1 A/Beijing) was assessed in an intranasal mouse model by addition of various amount of GEM particles (0, 0.03, 0.1 and 0.3 mg dry weight) to the HA. Mice received three vaccine doses, each with two weeks intervals and two weeks after the last booster immunizations, serum samples were analyzed. FIG. 1 shows that HA without adjuvant elicits only a low level of systemic IgG antibodies (5.0 μg/ml) through the intranasal route of administration. Addition of a small amount of GEM particles (0.03 mg) already increases this level by a factor 4. The best enhancement was found with the addition of 0.1 mg GEM particles to approximately 67 μg HA-specific IgG per ml, which did not further increase by the addition of more GEM particles. These results clearly show that admixing GEM particles with influenza HA enhances the antigen specific immune response in a dose dependent manner.

Example 2 Intranasal GEM Mixed with HA Compared with Intramuscular HA

A comparison was made between an intranasal HA+GEM vaccine and the traditional way HA vaccines are administered, i.e. HA without adjuvant administered through the intramuscular route. Mice received three doses of i.n. HA (5 μg H1N1 A/Beijing)+GEM (0.15 mg dry weight) or i.m. HA (5 μg) with intervals of two weeks between the doses. The HA-specific serum IgG titer was determined on samples taken two weeks after each immunization in order to compare the magnitude and the kinetics of the immune response of the intranasal and the intramuscular vaccines. FIG. 2 clearly demonstrates that both the magnitude and the kinetics of the i.n. HA+GEM vaccines is similar to that of the i.m. HA vaccine. There are no statistical significant differences between the responses of the i.n. and i.m. vaccines after each administration (each p-value>0.05).

Example 3 Intranasal GEM Mixed with HA Elicits Protective Responses

The protective capacity of influenza vaccines is determined by measuring HI titers. The HI titers were determined for all mice after the $1^{st}$ and $2^{nd}$ booster immunization with i.n. HA (5 μg H3N2A/Wisconsin), HA+GEM (0.3 mg dry weight), i.m. HA. FIG. 3 shows that both the conventional i.m. and the GEM adjuvanted i.n. vaccines reached comparable HI titers above $^2$log 6 after the $1^{st}$ booster immunization (p=0.2062). These titers increase in both cases to values between $^2$log 7 and $^2$log 8 with no significant differences between the two treatments (p=0.7611). I.n. immunization with the subunit vaccine alone induced low HI titers, even after two booster immunizations. Moreover, only 50% of the animals responded after immunization with i.n. subunit vaccine, while all animals responded in the two other vaccine groups. Since an HI titer above $^2$log 5.3 is considered to be protective in humans, these results indicate that a single boost is sufficient for i.n. GEM adjuvanted influenza vaccines to reach protective immunity. It is evident from the results that formulation of subunit vaccine with GEM particles induced a strong systemic immune response compared to both i.n. and i.m. immunization with subunit vaccine alone.

Example 4 Mucosal Immune Response of Intranasal GEM Mixed with HA

It has been reported previously that i.n. immunization may induce local mucosal immunity in respiratory tract i.e. the port of entry of influenza virus. The activation of the mucosal immunity primes the underlying B and T cells and results in secretion of sIgA at mucosal sites. Consequently, the influenza specific sIgA titers were determined in nasal and lung lavages of the mice (FIG. 4).

I.m. immunizations elicited sIgA levels in nasal and lung lavages below detection limits in most of the mice (only one out of eight mice showed a response in the nasal lavage). Similarly, the i.n. immunizations with subunit vaccine alone gave low sIgA titers in lung and nasal lavages (3/8 responders). In contrast, i.n. immunization with HA+GEM induced high sIgA titers in nasal and lung lavages of all mice.

In conclusion, i.n. immunization with HA+GEM induced a strong mucosal immune response at both the upper and lower respiratory tract.

Example 5 Phenotype of Immune Response of Intranasal GEM Mixed with HA

In order to evaluate the phenotype of the response i.e. the T-helper 1/T-helper 2 ratio (Th1/Th2), IgG subtypes, IFN-γ and IL-4 responses were determined.

IgG subtype profiling (FIG. 5) showed that i.n. immunization with subunit vaccine alone induced low IgG1, IgG2a and IgG2b responses. As previously reported [35, 36] i.m. immunization with subunit vaccine induced high IgG1 responses but little IgG2a and IgG2b, indicating an immune response biased towards Th2 response. In comparison to i.m. immunization, i.n. immunization with HA+GEM induced significant higher IgG2a (p=0.042) and IgG2b (p=0.030) and lower IgG1 (p=0.0135) responses. These results indicate that the antibody responses generated by i.n. HA+GEM vaccine is significantly more skewed towards a Th1 phenotype than the conventional i.m. vaccine.

The type of immune response (FIG. 6) was further evaluated by determining antigen specific IFN-γ and IL-4 producing splenocytes of the immunized mice. I.m. immunization with subunit vaccine resulted in a higher number of IL-4 producing cells than IFN-γ producing cells, indicating again a predominated Th2 response. I.n. immunization with subunit vaccine resulted in lower numbers of IL-4 producing cells but substantially higher numbers of IFN-γ producing cells (FIG. 6), resulting in a balanced Th1/Th2 response. The increase in IFN-γ producing T cells was even significantly (p=0.0373) more pronounced after i.n. immunization with HA+GEM, indicating a shift of the immune response from a balanced Th1/Th2 to a predominant Th1 response.

Example 6 Protection of Intranasal GEM Mixed with HA in Lethal Challenge Model The protective capacity of the immune responses generated with i.n. HA+GEM was evaluated in a lethal challenge model. Mice were immunized i.n. with PBS (mock immunization) or with HA alone (2 times), HA+GEM (2 times) or with HA+GEM (3 times). A comparison was made with the HA benchmark vaccine given intramuscularly. The HA in this experiment was derived from strain PR8 (H1N1). The dose was 5 µg HA per dose and 0.3 mg GEM per dose in case GEM was added to the vaccine. Vaccines were administered with 2 weeks intervals. Lethal challenge was done 3 weeks after the last booster immunization with a lethal dose of PR8. Protection against challenge was observed for the animals of group HA+GEM (i.n. 2 times; 9/9 survivors), HA+GEM (i.n. 3 times; 9/9 survivors) and HA benchmark control (i.m.; 9/9 survivors) [FIG. 7]. All animals within these groups showed no clinical signs after challenge (no lethargy, ruffled fur or hunch back posture) and survived up to day 14 until the end of the experiment. Protection correlated with the absence of body weight loss (not shown).

In contrast, most animals within groups HA i.n. and PBS (mock immunization, negative control) showed severe weight loss from day 3 and 4 onwards, respectively and were euthanized at day 5 to 8 post challenge due to severe clinical symptoms (weight≤85%, lethargy, ruffled fur, hunch back).

Determination of the viral titers in the lungs 4 days post challenge demonstrated that i.n. vaccinations with HA+GEM (2 or 3 times) lead to an approximately 1,000 to 10,000-fold reduction in viral titer in the lungs 4 days post challenge compared to the PBS negative control group (FIG. 8). A very limited reduction in viral titer (4-fold reduction) upon challenge was observed when HA was applied alone i.n., demonstrating that the adjuvanting properties of GEM are required to provide protection. Vaccination with HA+GEM (2 and 3 times) lead to an approximately 20 to 100-fold improvement in viral titer in the lungs compared to the benchmark positive control group (HA, i.m). Reduction of viral titers can result in reduced shedding of the virus and is considered to be an important factor in providing herd protection. The presence of local IgA in the mucosal linings of the respiratory tract and/or the better balanced Th1/Th2 type of the immune response generated by the i.n. HA+GEM vaccines as demonstrated in Examples 4 and 5 could explain the observed superiority of the protection as compared to the i.m. benchmark vaccine.

Example 7 Oral HA Mixed with GEM Elicit Protective Responses

The oral route of administration is attractive for vaccines because of it's convenience, but lacks often effectivity because antigens are inactivated or degraded. Oral administration of HA without adjuvants is known to be inadequate to elicit protective serum HI responses and/or mucosal IgA responses. The effect of adding GEM to HA in orogastric immunizations was analyzed in a mouse model. H3N2 A/Hiroshima subunit antigen HA (20 µg/dose) was used. The HA+GEM vaccines contained in addition 0.3 mg GEM per dose. Mice were immunized three times with two week intervals and samples of two weeks post final immunization were analyzed. Serum HI titers were determined to compare the protective capacity of the immunizations. As shown in FIG. 9, the oral immunization with the HA+GEM vaccine induced significantly higher (p<0.05) HI titers than oral immunization without GEM particles. In the oral HA+GEM group HI titers were reached above $^2$log 7 which is well above the protective cut-off level of $^2$log 5.3.

In addition, oral HA+GEM was able to raise considerable levels of mucosal IgA in the gastrointestinal tract (FIG. 10). Surprisingly, also a robust local IgA response in the respiratory tract was elicited in most of the animals.

These results demonstrate that also oral influenza HA vaccines mixed with GEM elicited protective systemic immune responses and in addition elicit potent mucosal responses including in the respiratory tract.

Example 8 Intramuscular HA Mixed with GEM Elicit Local Responses at Mucosal Surfaces Parenteral vaccines do usually not elicit the production of mucosally secreted IgA. In the analysis of mucosal samples of intramuscularly immunized mice we surprisingly found that mice that received HA+GEM secreted local IgA at several mucosal tissues such as the nose, lungs and vagina. Female mice were vaccinated three times (interval 14 days) intranasally or intramuscularly with a fixed amount of HA (5 µg B/Shangdong/7/97), with or without 0.3 mg GEMs. Two weeks after the last immunization, nose and vagina washes were performed and IgA titers were determined by specific ELISA assay.

The data in FIG. 11 show that intranasal administration of HA+GEM efficiently induced local IgA responses, evidenced as IgA titers in the nose washes. IgA titers were also induced distantly, evidenced as the appearance of IgA titres in vaginal washes. As expected intramuscular administration of HA alone does not induce relevant local IgA responses.

Surprisingly, intramuscular administration of HA+GEM induced relevant IgA titers, both in the nose and vagina with efficiencies approaching those reached after intranasal administration. Therefore, intramuscular administration of HA+GEM can be used to induce a mucosal immune response.

Example 9 Intramuscular Administration of HA Mixed with GEM Supports Significant Dose Sparing In order to determine whether the immune responses elicited by intramuscular GEM+HA allow for dose sparing of influenza HA antigen, mice were vaccinated twice with PBS (mock treatment), 1 µg HA (A/PuertoRico/8/34) without GEMs or with 0.04 µg HA (25 times less antigen) formulated with GEM (0.3 mg per dose). Two weeks after administration of the final dose, mice were challenged with mouse adapted A/PuertoRico/8/34. Five days post challenge, the animals were sacrificed, lungs were isolated and homogenized and viral titers were determined by endpoint titration on MDCK cells.

FIG. 12, panel A, shows that intramuscular vaccination of animals with 1 µg HA provides for reduction of viral load in the lungs of infected animals of more than a log as compared to the mock treated animals. However, HA+GEM provides complete protection against replication of influenza virus in the lungs of infected animals, as evidenced by complete absence of lung titers. These results demonstrate the superiority of the i.m. HA+GEM vaccine compared to the benchmark i.m. HA. The same level of protection as for the benchmark i.m. HA was achieved in the HA+GEM formulation containing only 0.04 µg HA (25 times less antigen) as shown in the panel B of FIG. 12, indicating that significant antigen sparing can be achieved by formulating intramuscular influenza vaccines with GEMs.

Example 10 Intranasal GEM-Based Hepatitis B Vaccines Elicit Strong Systemic IgG and Local IgA Responses in Mice Adult C57BL6 mice were immunized with GEM-based hepatitis B vaccines containing the HBsAg antigen. In this case HBsAg [5 µg] was mixed with GEM particles [0.15 mg dry weight]. An equal amount of HBsAg without GEM was also used for comparison. The vaccines were administered through the intranasal route. The commercial HepB vaccine VaxPro, which is adjuvanted with Alum, was administered subcutaneously as the benchmark vaccine. Serum IgG was measured after full immunization (3 doses, given with 10 day intervals). FIG. 13 clearly shows the adjuvant effect of the GEM particles in the intranasal vaccine. No HBsAg specific serum IgG response was measurable when HBsAg alone was intranasally administered. In contrast, HBsAg+ GEM elicited a vigorous HBsAg-specific serum IgG response with a dilution titer of 4.2. The intranasal GEM-HBsAg vaccine elicited similar HBsAg-specific IgG as the benchmark vaccine given through the subcutaneous route (p=0.2290). The activation of the mucosal immunity results in secretion of sIgA at mucosal sites. In this experiment the local secretion of HBsAg-specific sIgA was measured in washes of the vaccination sites (nasal) and in washes at a distant mucosal site (vaginal). FIG. 14 clearly shows that sIgA responses are only generated using the i.n. HBsAg+ GEM vaccine and not with the i.m. VaxPro vaccine. The i.n. HBsAg+GEM vaccine generates even secretion of sIgA at a distant mucosal site such as that of the vagina.

Example 11 Intranasal GEM-HBsAg Hepatitis B Vaccine in a Rat Model Elicits Protective Levels of Serum Antibodies Adjuvanted Hepatitis B vaccines were made by mixing the HBsAg antigen (25 µg) with GEMs (0.4 mg). For comparison, HBsAg antigen alone (25 µg) and a benchmark vaccine (VaxPro) that contains the same antigen formulated with Alum. Complete immunization consisted of three vaccine administrations given with 10 days intervals. The final sera were collected 14 days after the last booster. GEM-HBsAg and HBsAg were given intranasally. VaxPro was given through the intramuscular route. For Hepatitis B vaccines the correlates of protection are known. Antibody levels higher than 10 mIU/ml of blood serum are considered to be protective and are accepted as a surrogate marker for protection.

The blood sera of the fully immunized rats (4 Wistar rats per group) were analyzed for the levels of HBsAg-specific antibodies expressed in milli International Units per ml (mIU/ml). FIG. 15 summarizes the results. Intranasal HBsAg does not elicit a response at all. A high and protective level of antibody response (mIU/ml≥10) is obtained through the intranasal route when HBsAg is formulated with the peptidoglycan microparticles. The level of protection is similar with the benchmark vaccine VaxPro given through the intramuscular route (p=0.7715).

The results in examples 10 and 11 consistently demonstrate that strong systemic antibody and local antibody responses are evoked in intranasal GEM-based hepatitis B HBsAg vaccines, despite the fact that antigen is not actively bound to the GEM particle.

Example 12 Protectivity of Trivalent Pneumococcal Protein-Based GEM Vaccines

A comparison was made between intranasal pneumococcal protein-based vaccines formulated with GEMs either admixed or bound to the proteins. Three conserved pneumococcal proteins (PspA, CbpA, PdBD) were used in trivalent vaccines, GEM+P3 (mixed) and GEM-P3 (bound). Mice were immunized three times with these vaccines or with PBS as negative control (mock immunization) with 10 days intervals between the doses. Each GEM-based vaccine contained per dose 5 µg of each antigen and 0.3 mg GEM. Three weeks after the last booster immunization mice were challenged intranasally with a lethal doses S. pneumonia TIGR4 (serotype 4). Unprotected mice die within 72 h after challenge. Mice were followed up for 14 days post challenge. Mice were euthanized based on humane endpoints (>5.4×10³ colony forming units (cfu) per ml blood 48 h post challenge, weight ≤85%, lethargy, ruffled fur, hunch back) or at the end of the study. None of the mock immunized mice survived. It was surprisingly found that the group immunized with the GEM+P3 (mixed) vaccine showed a better survival (50%) than the group immunized with the GEM-P3 (bound) vaccine (20%) (see FIG. 16). These results clearly show that a GEM vaccine with the P3 proteins is more effective when these proteins are mixed to the GEM particles.

Example 13 Protectivity of Pentavalent Pneumococcal Protein-Based GEM Vaccines

A comparison was made between intranasal pneumococcal protein-based vaccines formulated with GEMs either admixed or bound to the proteins. Five conserved pneumococcal proteins (PspA, PsaA, CbpA, PpmA, IgA1prt) were used in pentavalent vaccines, GEM+P5 (mixed) and GEM-P5 (bound). Mice were immunized three times with these vaccines or with PBS as negative control (mock immunization) with 10 days intervals between the doses. Each GEM-based vaccine contained per dose 0.5 µg IgA1prt, 3 µg PsaA, 1.5 µg CbpA, 2 µg PpmA, 2 µg PspA and 0.3 mg GEM. Three weeks after the last booster immunization mice were challenged intranasally with a lethal doses *S. pneumonia* D39 (serotype 2). Unprotected mice die within 72 h after challenge. The health status 40 h after challenge was scored based on clinical symptoms (lethargy, ruffled fur, hunch back) and was taken as endpoint to measure the protective capacity of the vaccines. FIG. 17 shows that in the group immunized with the GEM-P5 (bound) vaccine 8 out of 10 mice remained completely healthy, while this was less for the GEM+P5 (mixed) vaccine (5/10) and minor for the negative control (1/10). These results clearly show that a GEM vaccine with the P5 proteins is more effective when these proteins are bound to the GEM particles.

The invention claimed is:

1. An adjuvanted influenza vaccine formulation, comprising an admixture of an immune-effective amount of (i) Gram-positive enhancer matrix (GEM) spherical peptidoglycan microparticles as an adjuvant, the GEM microparticles being obtained by acid treatment of a Gram-positive bacterium and (ii) at least one influenza virus antigen or antigenic preparation thereof, which antigen or antigenic preparation is not fused or otherwise covalently attached to the GEM microparticles.

2. The Vaccine formulation according to claim 1, comprising haemagglutinin antigen (HA), neuramidase antigen (NA) or a combination thereof.

3. The Vaccine formulation according to claim 1, comprising an influenza antigen or antigenic preparation thereof from at least two influenza virus strains, at least one strain being associated with a pandemic outbreak or having the potential to be associated with a pandemic outbreak.

4. The Vaccine formulation according to claim 1, wherein said vaccine formulation contains between 1 to 15 µg of HA per influenza strain.

5. The Vaccine formulation according to claim 1, wherein said microparticles obtained from food-grade bacterium, preferably a lactic acid bacterium, more preferably *L. lactis*.

6. The Vaccine formulation according to claim 1, comprising 0.01 to 0.1 milligram microparticles (dry weight) per microgram of antigen.

7. An intranasal dispensing device comprising the vaccine formulation according to claim 1.

8. The dispensing device according to claim 7 in the form of an aerosol or a drop delivery system.

9. A method for prophylaxis of influenza infection in a subject, wherein the method comprises administering to the subject the vaccine formulation according to claim 1.

10. The method according to claim 9, wherein the vaccine formulation is delivered intramuscularly.

11. The method according to claim 10, wherein the vaccine formulation is delivered intranasally by a dispensing device.

12. The method according to claim 11, wherein the dispensing device is an aerosol or a drop delivery system.

* * * * *